US012480127B2

(12) United States Patent
Chen et al.

(10) Patent No.: US 12,480,127 B2

(45) **Date of Patent: *Nov. 25, 2025**

(54) siRNA, MEDICAL COMPOSITIONS, AND METHODS FOR TREATING DIABETES USING THE SAME

(71) Applicant: PEKING UNIVERSITY, Beijing (CN)

(72) Inventors: Liangyi Chen, Beijing (CN); Wenzhen Zhu, Beijing (CN); Yi Wang, Beijing (CN)

(73) Assignee: PEKING UNIVERSITY, Beijing (CN)

( * ) Notice: Subject to any disclaimer, the term of this patent is extended or adjusted under 35 U.S.C. 154(b) by 25 days.

This patent is subject to a terminal disclaimer.

(21) Appl. No.: 18/359,858

(22) Filed: Jul. 26, 2023

(65) Prior Publication Data

US 2023/0383299 A1 Nov. 30, 2023

Related U.S. Application Data

(63) Continuation of application No. 17/663,826, filed on May 17, 2022, now Pat. No. 11,746,350, which is a continuation of application No. PCT/CN2021/086127, filed on Apr. 9, 2021.

(51) Int. Cl.

| | |
|---|---|
| ***C12N 15/113*** | (2010.01) |
| ***A61K 31/713*** | (2006.01) |
| ***A61P 3/10*** | (2006.01) |
| ***C12N 15/11*** | (2006.01) |

(52) U.S. Cl.

CPC ........ *C12N 15/1137* (2013.01); *A61K 31/713* (2013.01); *A61P 3/10* (2018.01); *C12N 15/111* (2013.01); *C12N 2310/14* (2013.01); *C12N 2310/3521* (2013.01)

(58) Field of Classification Search

CPC .......................... C12N 15/1137; A61K 31/713

See application file for complete search history.

(56) References Cited

U.S. PATENT DOCUMENTS

| | | | |
|---|---|---|---|
| 2005/0070594 | A1 | 3/2005 | Kauschke et al. |
| 2019/0008841 | A1 | 1/2019 | Cohen et al. |

FOREIGN PATENT DOCUMENTS

| | | | |
|---|---|---|---|
| CN | 104244938 A | | 12/2014 |
| CN | 104428009 A | | 3/2015 |
| EP | 1537864 A1 | | 6/2005 |
| JP | 2010265190 A | | 11/2010 |
| WO | 2006119647 A1 | | 11/2006 |
| WO | 2021067747 A1 | | 4/2021 |

OTHER PUBLICATIONS

International Search Report in PCT/CN2021/086127 mailed on Jan. 10, 2022, 8 pages.

Written Opinion in PCT/CN2021/086127 mailed on Jan. 10, 2022, 5 pages.

Xie, Hao et al., Dysregulations of Intestinal and Colonic UDP-glucuronosyltransferases in Rats with Type 2 Diabetes, Drug Metab. Pharmacokinet, 28(5): 427-434, 2013.

Mustapha Umar Imam et al., Effects of Brown Rice and White Rice on Expression of Xenobiotic Metabolism Genes in Type 2 Diabetic Rats, Int. J. Mol. Sci., 13: 8597-8608, 2012.

Yoshitaka Hasegawa et al., The Pharmacokinetics of Morphine and Its Glucuronide Conjugate in a Rat Model of Streptozotocin-induced Diabetes and the Expression of MRP2, MRP3 and UGT2B1 in the Liver, Journal of Pharmacy and Pharmacology, 62: 310-314, 2010.

Kristine Faerch et al., Insulin resistance is accompanied by increased fasting glucagon and delayed glucagon suppression in individuals with normal and impaired glucose regulation, Diabetes, 2016, 29 pages.

Richard M. Watanabe et al., Physiology Insights, The Genetics of Type 2 Diabetes and Related Traits: Biology, Physiology and Translation, 2016, 16 pages.

Leigh Perreault et al., Approaching Pre-diabetes, Journal of Diabetes and Its Complications, 28: 226-233, 2014.

N. Sattar et al., Novel biochemical risk factors for type 2 diabetes: pathogenic insights or prediction possibilities?, Diabetologia, 51: 926-940, 2008.

Wang, Thomas J. et al., Metabolite profiles and the risk of developing diabetes, Nature Medicine, 17(4): 448-454, 2011.

Aya Umeno et al., Multi-Biomarkers for Early Detection of Type 2 Diabetes, Including 10- and 12-(Z, E)—Hydroxyoctadecadienoic Acids, Insulin, Leptin, and Adiponectin, PLOS One, 2015, 16 pages.

Roger H. Unger et al., Glucagonocentric restructuring of diabetes: a pathophysiologic and therapeutic makeover, The Journal of Clinical Investigation, 122(1): 4-12, 2012.

Alain D. Baron et al., Role of Hyperglucagonemia in Maintenance of Increased Rates of Hepatic Glucose Output in Type II Diabetics, Diabetes, 36: 274-283, 1987.

G. M. Reaven et al., Documentation of Hyperglucagonemia Throughout the Day in Nonobese and Obese Patients with Noninsulin-Dependent Diabetes Mellitus, Journal of Clinical Endocrinology and Metabolism, 64(1): 106-110, 1987.

Roger H. Unger et al., Studies of Pancreatic Alpha Cell Function in Normal and Diabetic Subjects, The Journal of Clinical Investigation, 49: 837-848, 1970.

F. K. Knop et al., Impaired incretin effect and fasting hyperglucagonaemia characterizing type 2 diabetic subjects are early signs of dysmetabolism in obesity, Diabetes, Obesity and Metabolism, 14(6): 500-510, 2012.

(Continued)

*Primary Examiner* — Kevin E Weddington

(74) *Attorney, Agent, or Firm* — METIS IP LLC

(57) ABSTRACT

Compositions and methods for treating a subject are provided. The compositions may include a short interfering RNA (siRNA) molecule comprising a sense RNA strand and an anti-sense RNA strand, the sense and anti-sense RNA strands forming an RNA duplex. The method may include administering a medical composition including an agent to the subject, wherein the agent is configured to reduce uridine 5'-diphospho-glucuronosyltransferase (UGT) levels in the subject. The sense RNA strand or the anti-sense RNA strand may be 15 to 25 nucleotides in length. The sense RNA strand and the anti-sense RNA strand may be 70%-100% complementary.

11 Claims, 11 Drawing Sheets

Specification includes a Sequence Listing.

(56) References Cited

OTHER PUBLICATIONS

William L. Clarke et al., The Effect of Hyperglucagonemia on Blood Glucose Concentrations and on Insulin Requirements in Insulin-requiring Diabetes Mellitus, Diabetes, 27(6): 649-652, 1978.
J. W. Frank et al., Effects of Glucagon on Postprandial Carbohydrate Metabolism in Nondiabetic Humans, Metabolism, 47(1): 7-12, 1998.
B. Ahrén et al., Impaired Glucose Tolerance (IGT) is Associated with Reduced Insulin-induced Suppression of Glucagon Concentrations, Diabetologia, 44: 1998-2003, 2001.
Róbert Wagner et al., Non-suppressed Glucagon after Glucose Challenge as a Potential Predictor for Glucose Tolerance, Diabetes, 2016, 27 pages.
A. A. R. Starke et al., Elevated Pancreatic Glucagon in Obesity, Diabetes, 33: 277-280, 1984.
Dan Kawamori et al., Insulin Signaling in α Cells Modulates Glucagon Secretion In Vivo, Cell Metabolism, 9: 350-361, 2009.
E. Ferrannini et al., Association of Fasting Glucagon and Proinsulin Concentrations with Insulin Resistance, Diabetologia, 50: 2342-2347, 2007.
Roger H. Unger et al., Paracrinology of Islets and the Paracrinopathy of Diabetes, PNAS, 107(37): 16009-16012, 2010.
Xiong, Yusheng et al., Discovery of a Novel Glucagon Receptor Antagonist N-[(4-{(1S)-1-[3-(3, 5-Dichlorophenyl)-5-(6-methoxynaphthalen-2-yl)-1H-pyrazol-1-yl]ethyl}phenyl)carbonyl]-β-alanine (MK-0893) for the Treatment of Type II Diabetes, Journal of Medicinal Chemistry, 55: 6137-6148, 2012.
Russell A. Miller et al., Biguanides Suppress Hepatic Glucagon Signalling by Decreasing Production of Cyclic AMP, Nature, 2013, 6 pages.
Lawrence S. Phillips et al., We Can Change the Natural History of Type 2 Diabetes, Diabetes Care, 37: 2668-2676, 2014.
Philip Felig et al., Plasma Amino Acid Levels and Insulin Secretion in Obesity, The New England Journal of Medicine, 281(15): 811-816, 1969.
Christopher B. Newgard et al., A Branched-Chain Amino Acid-Related Metabolic Signature that Differentiates Obese and Lean Humans and Contributes to Insulin Resistance, Cell Metabolism, 9: 311-326, 2009.
Jens J. Holst et al., Glucagon and Amino Acids are Linked in a Mutual Feedback Cycle: The Liver a-Cell Axis, Diabetes, 66: 235-240, 2017.
Dalva Marreiro Rocha et al., Glucagon-stimulating Activity of 20 Amino Acids in Dogs, The Journal of Clinical Investigation, 51: 2346-2351, 1972.
Mahesha H. Gangadhariah et al., Cytochrome P450 Epoxygenase-derived Epoxyeicosatrienoic Acids Contribute to Insulin Sensitivity in Mice and in Humans, Diabetologia, 2017, 10 pages.
Guan, Hongping et al., Glucagon Receptor Antagonism Induces Increased Cholesterol Absorption, Journal of Lipid Research, 56: 2183-2195, 2015.
Makoto Osabe et al., Expression of Hepatic UDP-Glucuronosyltransferase 1A1 and 1A6 Correlated with Increased Expression of the Nuclear Constitutive Androstane Receptor and Peroxisome Proliferator-Activated Receptor α in Male Rats Fed a High-Fat and High-Sucrose Diet, Drug Metabolism and Disposition, 36(2): 294-302, 2008.
Xu, Jialin et al., UDP-Glucuronosyltransferase Expression in Mouse Liver is Increased in Obesity- and Fasting-Induced Steatosis, Drug Metabolism and Disposition, 40(2): 259-266, 2012.
Abdelkrim Khadir et al., MAP Kinase Phosphatase DUSP1 is Overexpressed in Human Obese and Modulated by Physical Exercise, the American Physiological Society, 2014, 43 pages.
Meenu Kesarwani et al., Targeting C-FOS and DUSP1 Abrogates Intrinsic Resistance to Tyrosine-kinase Inhibitor Therapy in BCR-ABL-induced Leukemia, Nature Medicine, 2017, 14 pages.
Mutsuhiro Takekawa et al., A Family of Stress-Inducible GADD45-like Proteins Mediate Activation of the Stress-Responsive MTK1/MEKK4 MAPKKK, Cell, 95: 521-530, 1998.
Ole-Morten Seternes et al., Dual-specificity MAP Kinase Phosphatases in Health and Disease, Molecular Cell Research, 1866: 124-143, 2019.
B. Ahrén, β- and α-Cell Dysfunction in Subjects Developing Impaired Glucose Tolerance, Diabetes, 58: 726-731, 2009.
Yao, Kang et al., LeucineinObesity: Therapeutic Prospects, Trends in Pharmacological Sciences, 2016, 14 pages.
Christopher J. Lynch et al., Branched-chain Amino Acids in Metabolic Signalling and Insulin Resistance, Nature reviews, 2014, 14 pages.
Richard Yan-Do et al., A Glycine-insulin Autocrine Feedback Loop eEnhances Insulin Secretion from Human β-cells and is Impaired in Type 2 Diabetes, Diabetes, 2016, 41 pages.
Guillaume Kraft et al., Glucagon's Effect on Liver Protein Metabolism in Vivo, the American Physiological Society, 2017, 37 pages.
Ann M. Ingalls et al., Obese, A New Mutation in the House Mouse, the Journal of Heredity, 1950, 2 pages.
Chen, Hong et al., Evidence That the Diabetes Gene Encodes the Leptin Receptor: Identification of a Mutation in the Leptin Receptor Gene in db/db Mice, Cell, 84: 491-495, 1996.
Maria Sorhede Winzell et al., The High-fat Diet-fed Mouse: A Model for Studying Mechanisms and Treatment of Impaired Glucose Tolerance and Type 2 Diabetes, Diabetes, 53(3): S215-S219, 2004.
D. R. Matthews et al., Homeostasis Model Assessment: Insulin Resistance and β-cell Function from Fasting Plasma Glucose and Insulin Concentrations in Man, Diabetologia, 28: 412-419, 1985.
Maria Antonietta Pellegrino et al., Effects of Voluntary Wheel Running and Amino Acid Supplementation on Skeletal Muscle of Mice, Eur J Appl Physiol, 93: 655-664, 2005.
Giuseppe D'Antona et al., Branched-Chain Amino Acid Supplementation Promotes Survival and Supports Cardiac and Skeletal Muscle Mitochondrial Biogenesis in Middle-Aged Mice, Cell Metabolism, 12: 362-372, 2010.
Daehwan Kim et al., HISAT: A Fast Spliced Aligner with Low Memory Requirements, Nature Methods, 2015, 6 pages.
Mihaela Pertea et al., StringTie Enables Improved Reconstruction of A Transcriptome from RNA-seq Reads, Nature Biotechnology, 2015, 8 pages.
Michael I. Love et al., Moderated Estimation of Fold Change and Dispersion for RNA-seq Data with DESeq2, Genome Biology, 2014, 21 pages.
Huang, Dawei et al., Systematic and Integrative Analysis of Large Gene Lists Using DAVID Bioinformatics Resources, Nature Protocols, 4(1): 44-57, 2009.
Minoru Kanehisa et al., KEGG Mapper for Inferring Cellular Functions from Protein Sequences, Protein Science, 2019, 8 pages.
Zhang, Lifang et al., Dysregulations of UDP-glucuronosyltransferases in rats with valproic acid and high fat diet induced fatty liver, 721: 277-285, 2013.
Chang, Wen-Chang et al., Protective Effect of *Ruellia tuberosa* L. Extracts against Abnormal Expression of Hepatic Detoxification Enzymes in Diabetic Rats, The Royal Society of Chemistry, 8: 21596-21605, 2018.
Zheng, Shuquan et al., siRNA Knockdown of RRM2 Effectively Suppressed Pancreatic Tumor Growth Alone or Synergistically with Doxorubicin, Molecular Therapy: Nucleic Acids, 12: 805-816, 2018.
The Extended European Search Report in European Application No. 21895926.0 mailed on Jul. 10, 2023, 10 pages.
Fan, Lei et al., Fibroblast Growth Factor-1 Improves Insulin Resistance via Repression of JNK—Mediated Inflammation, Frontiers in Pharmacology, 2019, 10 pages.
Eric Lévesque et al., Effect of Fibroblastic Growth Factors (FGF) on Steroid UDP-glucuronosyltransferase Expression and Activity in the LNCaP Cell Line, J. Steroid Biochem. Molec. Biol, 64(1/2): 43-48, 1998.
Yang, Na et al., UDP-glucuronosyltransferases (UGTs) and Their Related Metabolic Cross-talk with Internal Homeostasis: A Systematic Review of UGI Isoforms for Precision Medicine, Pharmacological Research, 121: 169-183, 2017.
David B. Buckley et al., Induction of Mouse UDP-Glucuronosyltransferase mRNA Expression in Liver and Intestine

(56) References Cited

OTHER PUBLICATIONS by Activators of Aryl-Hydrocarbon Receptor, Constitutive Androstane Receptor, Pregnane X Receptor, Peroxisome Proliferator-Activated Receptor α, and Nuclear Factor Erythroid 2-Related Factor 2, Drug Metabolism and Disposition, 37(4): 847-856, 2009.

SEQUENCE LISTING

```
Sequence total quantity: 27
SEQ ID NO: 1            moltype = RNA  length = 19
FEATURE                 Location/Qualifiers
source                  1..19
                        mol_type = other RNA
                        organism = synthetic construct
SEQUENCE: 1
ggttactgta gttcacaaa                                         19

SEQ ID NO: 2            moltype = RNA  length = 21
FEATURE                 Location/Qualifiers
source                  1..21
                        mol_type = other RNA
                        organism = synthetic construct
SEQUENCE: 2
tttgtgaact acagtaacct c                                      21

SEQ ID NO: 3            moltype = RNA  length = 19
FEATURE                 Location/Qualifiers
source                  1..19
```

```
                      mol_type = other RNA
                      organism = synthetic construct
SEQUENCE: 3
ggactttgat acaatgtca                                              19

SEQ ID NO: 4          moltype = RNA  length = 21
FEATURE               Location/Qualifiers
source                1..21
                      mol_type = other RNA
                      organism = synthetic construct
SEQUENCE: 4
tgacattgta tcaaagtcca c                                           21

SEQ ID NO: 5          moltype = RNA  length = 19
FEATURE               Location/Qualifiers
source                1..19
                      mol_type = other RNA
                      organism = synthetic construct
SEQUENCE: 5
cattgtttct ggttattaa                                              19

SEQ ID NO: 6          moltype = RNA  length = 21
FEATURE               Location/Qualifiers
source                1..21
                      mol_type = other RNA
                      organism = synthetic construct
SEQUENCE: 6
ttaataacca gaaacaatgg c                                           21

SEQ ID NO: 7          moltype = RNA  length = 19
FEATURE               Location/Qualifiers
source                1..19
                      mol_type = other RNA
                      organism = synthetic construct
SEQUENCE: 7
gagtaaagat gatcttgaa                                              19

SEQ ID NO: 8          moltype = RNA  length = 21
FEATURE               Location/Qualifiers
source                1..21
                      mol_type = other RNA
                      organism = synthetic construct
SEQUENCE: 8
ttcaagatca tctttactca a                                           21

SEQ ID NO: 9          moltype = RNA  length = 19
FEATURE               Location/Qualifiers
source                1..19
                      mol_type = other RNA
                      organism = synthetic construct
SEQUENCE: 9
gagatttgat ggtaagaaa                                              19

SEQ ID NO: 10         moltype = RNA  length = 21
FEATURE               Location/Qualifiers
source                1..21
                      mol_type = other RNA
                      organism = synthetic construct
SEQUENCE: 10
tttcttacca tcaaatctcc a                                           21

SEQ ID NO: 11         moltype = RNA  length = 19
FEATURE               Location/Qualifiers
source                1..19
                      mol_type = other RNA
                      organism = synthetic construct
SEQUENCE: 11
ggttactgta gttcacaaa                                              19

SEQ ID NO: 12         moltype = RNA  length = 21
FEATURE               Location/Qualifiers
source                1..21
                      mol_type = other RNA
                      organism = synthetic construct
SEQUENCE: 12
tttgtgaact acagtaacct c                                           21

SEQ ID NO: 13         moltype = RNA  length = 19
FEATURE               Location/Qualifiers
```

```
source                  1..19
                        mol_type = other RNA
                        organism = synthetic construct
SEQUENCE: 13
ggactttgat acaatgtca                                                19

SEQ ID NO: 14           moltype = RNA  length = 21
FEATURE                 Location/Qualifiers
source                  1..21
                        mol_type = other RNA
                        organism = synthetic construct
SEQUENCE: 14
tgacattgta tcaaagtcca c                                             21

SEQ ID NO: 15           moltype = RNA  length = 19
FEATURE                 Location/Qualifiers
source                  1..19
                        mol_type = other RNA
                        organism = synthetic construct
SEQUENCE: 15
cattgtttct ggttattaa                                                19

SEQ ID NO: 16           moltype = RNA  length = 21
FEATURE                 Location/Qualifiers
source                  1..21
                        mol_type = other RNA
                        organism = synthetic construct
SEQUENCE: 16
ttaataacca gaaacaatgg c                                             21

SEQ ID NO: 17           moltype = RNA  length = 19
FEATURE                 Location/Qualifiers
source                  1..19
                        mol_type = other RNA
                        organism = synthetic construct
SEQUENCE: 17
gagtaaagat gatcttgaa                                                19

SEQ ID NO: 18           moltype = RNA  length = 21
FEATURE                 Location/Qualifiers
source                  1..21
                        mol_type = other RNA
                        organism = synthetic construct
SEQUENCE: 18
ttcaagatca tctttactca a                                             21

SEQ ID NO: 19           moltype = RNA  length = 19
FEATURE                 Location/Qualifiers
source                  1..19
                        mol_type = other RNA
                        organism = synthetic construct
SEQUENCE: 19
gagatttgat ggtaagaaa                                                19

SEQ ID NO: 20           moltype = RNA  length = 21
FEATURE                 Location/Qualifiers
source                  1..21
                        mol_type = other RNA
                        organism = synthetic construct
SEQUENCE: 20
tttcttacca tcaaatctcc a                                             21

SEQ ID NO: 21           moltype = DNA  length = 19
FEATURE                 Location/Qualifiers
source                  1..19
                        mol_type = other DNA
                        organism = synthetic construct
SEQUENCE: 21
ggaccgagct gtcttctgg                                                19

SEQ ID NO: 22           moltype = DNA  length = 21
FEATURE                 Location/Qualifiers
source                  1..21
                        mol_type = other DNA
                        organism = synthetic construct
SEQUENCE: 22
cacacagacc aataggaacc c                                             21

SEQ ID NO: 23           moltype = DNA  length = 19
```

```
FEATURE                Location/Qualifiers
source                 1..19
                       mol_type = other DNA
                       organism = synthetic construct
SEQUENCE: 23
gtgctggtgt ggcctacag                                           19

SEQ ID NO: 24          moltype = DNA  length = 19
FEATURE                Location/Qualifiers
source                 1..19
                       mol_type = other DNA
                       organism = synthetic construct
SEQUENCE: 24
attgctcggc ccaatgagg                                           19

SEQ ID NO: 25          moltype = DNA  length = 20
FEATURE                Location/Qualifiers
source                 1..20
                       mol_type = other DNA
                       organism = synthetic construct
SEQUENCE: 25
aacggcagca tttataaccc                                          20

SEQ ID NO: 26          moltype = DNA  length = 20
FEATURE                Location/Qualifiers
source                 1..20
                       mol_type = other DNA
                       organism = synthetic construct
SEQUENCE: 26
cgatctgcag acacacactg                                          20

SEQ ID NO: 27          moltype = DNA  length = 9865
FEATURE                Location/Qualifiers
source                 1..9865
                       mol_type = genomic DNA
                       organism = Mus musculus
SEQUENCE: 27
gcaagatgtc tatgaaacag gcttcagttt ttctgttgat acagttcata tgctatatta  60
gacctggagc ctgtgggaaa gtgctggtgt ggcctacaga atacagccat tggataaata  120
tgaaaataat cctggatgaa cttgtccaga gaggtcatga cgtcaccgtt ctcatatctt  180
ctgcttccat cctcattggg ccgagcaatg aatcttctat taattttgaa atttattctg  240
caccctttgag taaagatgat cttgaatatg cttttgaaaa atgggtagga aactggacat  300
acgaattaaa aaaacttcca ttttggacat cttattcaaa actgcaaaaa atctccagtg  360
aatattcaga catgattgaa agtttctgca aagcagtagt ttggaacaag agcctcatga  420
aaaaactcca aggatctaag tttgatgtcg ttctagcaga tgccttggtt ccctgtggtg  480
agctgctatc agaactgctt aagacacctt tagtatacag tctccgcttc tgtcctggat  540
acaaatgtga aaagtacagt gggggccttc cactcccccc ttcctatgtg cctgtggttc  600
tgtcagaact aagtgaccac atgacatttg cagaaagggt gaagaatatg ttgcaggtgt  660
tgctttttga cttttggttt caaacattta acgagaaatc ctggaatcag ttttacagtg  720
atgttctagg taaactgtgc ctttcattgt tactgtgaaa tcctgacttg atgttttttt  780
gaatgagaat gtgtataggt gaatataaag gcatagaatg agattcttaa ttgtgagctg  840
atagagtaaa aatagaagag aatcaaatag gctcttagca aggcaaaata ctgcagagta  900
attatacaga acacttcaga aattactaac catgcaaaat tagacaagga agatttctct  960
tggtgatcat ttgatctgct ctacattgtc taagtataag aaactccagg tttcattgag  1020
tgctttaata tctgtaaatg agaacactac agagtcataa ttcattacca caactatttg  1080
tgtagcactg aagaaaacac atttccttaa gacatttact cacttagaaa ttaaaacatt  1140
tatcaagaat gtcctgaaag cttattcaca attaaattgt accactagaa ccagaaacag  1200
tcaaggcaac ttgattttct tagaatttga gttggatcat atctataaaa cttaatctta  1260
aagccttaaa tcttgataga aatgcatagg tttttattat tttcaaaata ccttttcatt  1320
aaataaaata ttacctaatt tattaggaga aacagtttaa atattaactg cttatacaaa  1380
tacccagcta taactttgag atatacaact aagttagtga tactagtctc ctgtaacgga  1440
catagtacag cagggataaa agaaaattag tcattcctta ccaattatca cattgcattt  1500
caagaatcag aaaccaaaag catagctact aaaatgtgta aaatagacta aatattctac  1560
aaaagctgtg tttctaagca ttttcaagca cctttgcaag agcaaaattt caaatttatt  1620
ggtgcaacgt tggaaatcaa tgtaattttc acacaatatt tatgttaata caattatatc  1680
ataaatcata actggaacat tttaaattgc ttgtctacat gacctcaact cattgcagaa  1740
atcacatgct ttattccaga caaactcctt tcaccatagt gtatttgttt ttggttttgg  1800
ggtgcaggga gacctacaac attaactgag atgatgggga aggcagacat atggctcgtt  1860
cgaaccttct gggacttgaa atttcctcac cctttcttgc ctaattttga ctttgttgga  1920
ggactccatt gtaaaccagc caaaccactg cctaaggtaa ctctacattg tttcccttgg  1980
taaactgttt ttccttttca tggaaacaat tcttaaccac tatttccaga tgtttggttt  2040
tatgaaacat atatcaagtg gattagaact ctctgacaat taagatatac attatttcct  2100
tacatctctg aatcttctta ctcttaagca aagtattata ccactttaga atgtggtcag  2160
tgatttaaag gtgtttaggt aactcataaa agagaattta tgctctcttc aagaacatat  2220
agtaaatgcc agagacgtgt tgaacagcta aagaaataaa gaatcaatat cttcactaaa  2280
tagaaattgt attctacttg gaaacattat agtgatgaag agatgttata tacactgtga  2340
caaacgttat acattgttat attagataaa cagataagtt gaagatatat ccaacagaga  2400
tgagatgtaa tgtcctagaa tccttgtgaa gttacaatga cctagccaat gtacagggtt  2460
agattaatga atgaaaagaa gagaggaaaa atagaaaatt gaaacaacca ttgaaagaat  2520
```

-continued

```
gacagactta gataagcagg acgatgacat ggcaggcagg agtttttgga cagcttcatg  2580
tatgcatgtt ccacacatgg ctctctttta acctttccac ttccttggag tctttctacc  2640
cttaggttct gcagggattt attttttgtc tttgtagttt ccacatgcaa aagaaaaacaa  2700
cacttatctt tctgtttctg gcttattgat taatctcctg tcctctaaac aatagctatt  2760
ttcctaaatt atttaataat aataacattt ttctatctga gtaaaacaca attatgtata  2820
tttaccaaca ctttgataca cattgatcac ttgaagaata tctaagctaa tcctatatag  2880
gggaattttg aataatgatg taataaacat tattatgtag atttttcact tgcaattatt  2940
tccttcagat atcaccaaag agtggcatag gttaactgta tgtaacacat taatgttatt  3000
tatatcaaga cgcttattta tgtattttat ctaattttac atttccaaat atgataaatg  3060
cataaatgtt caatttccat attatctgta ggagcatttt tatagtacat acatttttgt  3120
gacattcatg ataagtggat tatgatggaa tattgatata ttttgaattt atttttttaa  3180
tagctgacat tattgaaaga ttttcagata attgtaagct atttaaatct gagggaacaa  3240
ctactttgga tcatttgcct aagttaattg aattcttatt tcttctgatg ttagtttgtt  3300
tttttaatta gcatactctc ttaaaaattt atgaatatta cacaactctt tagagagtct  3360
cttcattttg atagattttt ttgttcttca taagctttta ctataaggta ctcctatttt  3420
tcaattccca aattactccc aatgctactg tggttattca atacattact gctttttatt  3480
ctatgtcatg gagtttctct tcttttttcc ctatttttat gtagtagaaa cacattactt  3540
ttatttagaa tgtactaaag ataatttctt ttttttcaat gtgagaatac ataatttttt  3600
caattaatta atttatttat gccccaaatg ttgcctacat cgtggtcccc ctcttagagt  3660
tcttctctat ccctcatctc cctctatctc tccttcccta catttcttct tcttttctat  3720
tccctccttt gctgctcgtc cttctcattt ctctcaaaga aaccacaaaa aagaaaatca  3780
aagaaatgaa cttaaaaaaa taagaccaaa aatattccag caaaacgaaa ggaaagaaaa  3840
agcacacata agatttaata taaataaata aataaataaa taaataaata aataaaaaca  3900
tggcatttat tttaggtggc taactattcc tgggcttggg acctcctctg gtgtatgatt  3960
gatttaccca gtcactactg gggaaagctg gttttcccct ttgttatcag ataccacttg  4020
caaatagctt cttagttaga agtggaagtc catgaacatt ttctattctg tgcgcaggaa  4080
cttcatctgc cttgaacctg ggcaggtctt agacatgctg ctacagtctc tgtgagttta  4140
tatgagcatc agtcttatta tgcctggtag accctgggat gtcattcatc ccctctggat  4200
cttataaact ttctccctcc tactcatgat ggtttgaaaa tacctcctaa tgaaactcta  4260
aatttcaata actctactga caataatttt ttactctaat tttcttatgt tggtaaattg  4320
tactatagca caaatgtact ctccatgaac acatgactgc tgaggcaatg gatacactgg  4380
tctcactaaa ataattccag taattacatt atttcctctg gtaatgtttg tctcagttcc  4440
ttagacagtg cttcccaggc agccattaat ttgtgatgtc acaactgtct tcataggaaa  4500
tggaagaatt tgttcagagc tctggagaac atggtgtggt ggtgttttct ctgggatcaa  4560
tggttaaaaa cattaaagaa gaaaaggcca atgtagttgc ttctgctctt gcccagattc  4620
cacagaaggt aacataaaga gttcactggg tggacaaatg tattgtaagt ctattgaact  4680
ctgaaaggat tgcagtagga aaaactgctg tgaaatataa agtaaggggt tctttcctat  4740
gaatctcaaa caccacatta aaaagaaaag aatgaattgc agaagataaa atattagtct  4800
ggttctgatt gacattataa cctgaaggat cacacttaga tccagcatgg ttgtgcatac  4860
ctgacctgtt ggagcttaaa gagctgaggt aggtcttttt cttcatattt acaaccagtt  4920
tacacttcat gttgattccc aggcttttct gagtcattca gtgtgtcagt gtctcaaaag  4980
gagagaagta aaagaaagaa aggatggaag gaaggagaaa cagaagggag atgtacagtt  5040
atgaggaata ttatgctgag gctggaaagg tgcctcagtg atgcattaag aacacaggct  5100
gctcttccag aggaactgga cttgattgct aggacttaca tagtagctca taagtatccc  5160
caactcaatt gccagggaat ctcatgtgtt cttcatgccc cagacagaac agtcacagtg  5220
catgcactga attacatgca ggcaaaagat catatacata aaatgaaaca aaaatatctg  5280
taaagaaaga ggaaaaatatc ttcttgccag tgactgatgt aggaaaacat aagagaaaag  5340
ataaaaaaaa taggtgctga ctctgcagtg aactcaggat tataaaatta tgaactcatc  5400
aacaggaact atgcttctag cacatcagat aaacatgttt ttctggatgg tgaaagaggc  5460
tgtaatttaa gatggagtct tatgtaagca aggacagtgt gggaagaatc cagcagctcc  5520
caacgtcata aactctattg ttgaattact tcctaaaagc agaagtcttt tgatgtttgt  5580
aaactacatt tactctatta cttgatactg ataccgccta ttgtggagat aattttttat  5640
cttacaaaac acaaagcata cagaaagtaa agactgacag ttattattcc agtttgtgaa  5700
acttccttgt acgttagaac tcagtttgat actagacatg aaatgtattc aggacaattc  5760
aaagcatatt ttcaattttc ctattgacaa ttgtttcttt tttgtttttg tttttgtttt  5820
tgagacaatt tttcatggac agtcgttaat agactttatc tgaaatgaag catacttgct  5880
agtaagaaag aaattatttt tagaaatggg aaattatatc atggtatatt atgaatcaaa  5940
ataaacctaa ttataatgaa tagctgaaag aacacggaaa tataggtaaa actatgtggc  6000
tatgatttta aaagatgcaa tattgagatt atatgtaata tttacatata tcctatatat  6060
aggattatat atgaaatata cataatcaca taatcataaa atattactaa tttaacactg  6120
ttttcccagt aaggattata ttaactctct aaaaatgtca tgtatacaag aatttgtcgt  6180
taattatcag atatataaaa attgtaacac agaagtggat gctcacagtc agctcttgga  6240
tggatcacag ggctcccaat ggaggagcta gagaaagtat ccaaggagct aaagggatct  6300
gcaaccctat agatggaaca acattatgaa ctaaccagta ccccagagct cttgactcta  6360
gctgcatatg tatcgaaaga tgacctagtc ggccatcact ggaaagagag gcccattgga  6420
cttgcaaact ttatatgccc cagtacaggg gaacaccagg gccaaaaagg gggagtgggt  6480
gggtagggga gtggggggcg gtatggggga cttttgggat agcattggaa atgtaaatga  6540
ggaaaatacc taataaaaaa ttaaaaaaac agaaatttta aaaaatgtat aattaaatgg  6600
catgctcaag ttattaggaa gccatgtata gaaaatgtat tatttatttc agtcttttaa  6660
tatctcatac tagtttagat ttcccttcta ttaaatttta tagtccatca tctggataat  6720
gttcaactga gtaatctcaa ttctctagaa tcaaaatatg ccaaagcctt ggatttcttt  6780
aattaaataa ggtagtgtct gtgtgtaaca ggttctgtgg agatttgatg gtaagaaacc  6840
agacacctta ggatccaaca ctcggctcta caagtggatc ccccagaatg accttcttgg  6900
taaggcaaag ttccactaca gctttggggc tatagtaata tacttatttg agaacagccc  6960
ccttctgagc cttcatattc cccctgtctt taatattatg atcaataatt atgtaaaact  7020
tcttctcact gcaggtcatc caaaaaccaa agcttttata gctcatggtg gaaccaatgg  7080
catctatgag gcgatctacc atggcattcc tattgttggt attcccttgt ttggggatca  7140
acctgataat attaaccaca tagtagccaa gggagcagct gttagagtgg actttgatac  7200
aatgtcaact acagaccttc tcactgcctt gaagactgtc attaatgacc cttcgtgagt  7260
```

-continued

```
ctatttgttg tttgtttcct tgtttgaagt tgttttggtt tttttaagg tttttttttc  7320
ttttcttttc ttttttgttt tgtactatgt aaccacaaga ccagccaata actgatatag  7380
gtctgcttgc ttctgtctcc tgagtgctag aattaaaact atgtgcattc acgcttgatg  7440
gtgaataact attcctttga aaatattgct agattcacaa catcagattg atttttatcc  7500
tatttgaagg agaataattt tgaataactt tgtgatattg catgtctgaa atatgtgctt  7560
actttaacaa taaagatacc ttgaatttaa gtttcaataa atgagacatg ataagtctta  7620
aactattcta tatacataaa taatatcaca aatatatgtc tattggtaac aaggacacta  7680
tttcaagata gaatgtacat agtattcatg aaccatgatc ttaaatgaaa agttaaacat  7740
ttacccatat tttctgaagt tataaaactt ttggtaaaac tttaatttct ataatgatat  7800
gtgatattgc ataaccagta ctgaagaaat gagagagagt attaaattat taccataccc  7860
agagaacact gttggtagtt tcaaggtatt ccaatagaca aatgtaccta atgagaatat  7920
ccagaggcaa aataacagga gaaagtgcac ctggttcttc catacacagt ctcctagtcc  7980
aggaacacaa ttacattgct ttccatccag tcagaagtct gctggaaatt ctgttcaagg  8040
aagaataata acttagcaag tgttttcaaa acatgaatct gattataaaa agaaattagg  8100
aaacagagat agaagagaag aggagaaacc aaaactagag aggagatatc cagcatgaga  8160
tatgaccctg tagagtttaa aagaattcag tgtccacttc ttttcttaaa acttacacac  8220
acatacacac acacacacac acacacacac acacactttc tcttgccaat gtttgaaata  8280
ttgctcaact tcaaattaaa aataagtatt ctatggggaa taaagcaaaa ataagccaag  8340
tgtacctgag gagctggtat acaaggtaag ctcattagtt ggaggtaaat tcaggacttc  8400
attaagacca gtgtcaacta cacaccaagt tcaaaaaaaa acctgtacta aacaagactg  8460
tttcactgac ttccctgtca ctcaactgtc ctccctatca cctcataaaa catagtactt  8520
gtgtgggaag tttatgccat tcattttgag actcttgtgg gacttttccc caaaccaata  8580
aatgttaggg aagtcgacaa attagcttta attttagttg catgcattgt cctttcagct  8640
ataaagagaa tgccatgaga ttatccagaa tccaccatga ccagccaatg aagcccttgg  8700
accgagctgt cttctggatc gagtatgtca tgcgcaacaa gggagccaag caccttcgcc  8760
cagctctgca tgaccttacc tggttccagt accactctct ggatgtgatt gggttcctat  8820
tggtctgtgt ggtagctgtg gtattcatca ttgcaaaatg ttgcctcttt tgttgccata  8880
agactgctaa catgggaaag aagaaaaaag agtagcttca tgaaggctga agcagagagt  8940
cctgagagat gagcctctgc cagctgcttc cagcagaaac ctgttgtctg tcccaggtgc  9000
cttccctctg aaacaagaca gggtcaggac ttcattaaag atagctctca tagatgcact  9060
atatgttgaa tgcacgtaag gatttatgca agctatacac tcagagctct agaagcaaaa  9120
ttgtgtgttc agtttagaat gttttaatgt aaatgaggaa ctatacccaa caacaatcac  9180
tgaggttact gtagttcaca aaatttgcat aggcataaag cctttgaaaa acctctctaa  9240
atattagtta atttttatg ctctgtcttc atttaatgaa cttatttttc ttcccttcct  9300
tttttcttct ctttcatttt tttttgtatt gctcataaat aatagcgttc aggtacagaa  9360
catttgaaat agactcactt ttccatcaat ataaggaaag ccattgtttc tggttattaa  9420
ttgggtacag caaacttcca acaaatattt cctaaagggc ctgtggtgga ggctactctc  9480
cttcaatcag aagccttttt cagacactaa tcttcaagca tttactctta ctgctcctga  9540
cataaattcc agtacttggg agttcttagg cttggcaaga ttattgattt attttccttc  9600
ttatctctta ctcacaactg acctgaacac tgtcattctc attctgcctt ttgaagtaga  9660
tttaagctgc caaatgtccc attctctctc gctttgaaag tacacatcca agagaagatt  9720
atctttttaa gtcataccat cacctagctc atgttatatt tcgtatctga aatatccccc  9780
acagacacac aatgtacttt gctgattttg tttaactcat tcatacagaa tttcttacct  9840
tgattcaata aaatgttaaa atctt                                        9865
```

siRNA, MEDICAL COMPOSITIONS, AND METHODS FOR TREATING DIABETES USING THE SAME

CROSS-REFERENCE TO RELATED APPLICATIONS

This application is a Continuation of U.S. application Ser. No. 17/663,826 filed on May 17, 2022, which is a Continuation of International Application No. PCT/CN2021/086127, filed on Apr. 9, 2021, the contents of which are hereby incorporated by reference to its entirety.

SEQUENCE LISTING

The instant application contains a Sequence Listing which has been submitted electronically in XML format and is hereby incorporated by reference in its entirety. The XML copy, created on Jul. 24, 2023, is named "20317-0003US01-sequence Listing" and is 34,493 bytes in size.

TECHNICAL FIELD

The present disclosure generally relates to RNA, and in particular, to a short interfering RNA (siRNA), medical compositions, and methods for treating diabetes.

BACKGROUND

Diabetes is one of the four major non-communicable diseases in the world. According to a report by the World Health Organization, about 422 million people in the world suffer from diabetes, and 1.6 million people die of this disease each year. Diabetes occurs when the pancreas cannot produce enough insulin or when the body cannot effectively use insulin to regulate blood glucose.

Diabetes is difficult to treat, and conventional medications often result in huge medical expenses, psychological pain, and physical torture. People have made significant efforts to find new targets and develop new drugs for diabetes, but new discoveries and treatments are still in need.

One of the candidate categories of new drugs is small interfering RNA (siRNA), which has been investigated as novel classes of therapeutic agents for the treatment of a wide range of disorders. Therapeutic approaches based on siRNA involve the introduction of a synthetic siRNA into the subject to elicit RNA interference (RNAi), thereby inhibiting the mRNA expression of a specific gene to produce a gene silencing or inhibiting effect.

Therefore, it is desirable to provide for new treatments of diabetes (e.g. siRNA drugs) that are economical, long-lasting, or less physically damaging.

SUMMARY

According to an aspect of the present disclosure, a method of treating a subject suffering from diabetes is provided. The method may include administering a medical composition including an agent to the subject. The agent may be configured to reduce uridine 5'-diphospho-glucuronosyltransferase (UGT) levels in the subject.

In some embodiments, the agent may be configured to reduce UGT levels by inhibiting an expression of Ugt2b1 gene.

In some embodiments, the agent may be an inhibitory RNA.

In some embodiments, the inhibitory RNA may be a short interfering RNA (siRNA).

In some embodiments, the siRNA may include a sense RNA strand and an anti-sense RNA strand. The sense and anti-sense RNA strands may form an RNA duplex. The sense RNA strand or the anti-sense RNA strand may be 15 to 25 nucleotides in length. The sense RNA strand and the anti-sense RNA strand may be 70%-100% complementary.

In some embodiments, the siRNA may include a sense RNA strand and an anti-sense RNA strand. The sense RNA strand may have a nucleotide sequence having at least 80% similarity with SEQ ID NO. 1. The anti-sense RNA strand may have a nucleotide sequence having at least 80% similarity with SEQ ID NO. 2. The sense RNA strand may have a nucleotide sequence having at least 80% similarity with SEQ ID NO. 3. The anti-sense RNA strand may have a nucleotide sequence having at least 80% similarity with SEQ ID NO. 4.

In some embodiments, the sense RNA strand may have a nucleotide sequence of SEQ ID NO. 1. The anti-sense RNA strand may have a nucleotide sequence of SEQ ID NO. 2.

In some embodiments, the sense RNA strand may have a nucleotide sequence of SEQ ID NO. 3. The anti-sense RNA strand may have a nucleotide sequence of SEQ ID NO. 4.

In some embodiments, the sense RNA strand and/or the anti-sense RNA strand may include modified nucleotides at about 25%-100% of nucleotide positions.

In some embodiments, the modified nucleotides may include one or more of an O-methyl modified nucleotide, a phosphorothioate modified nucleotide, or a fluoro modified nucleotide.

In some embodiments, the sense RNA strand may include a modified RNA strand having a nucleotide sequence of SEQ ID NO. 11 or SEQ ID NO. 13, in which "m" represents O-methyl modification, "s" represents phosphorothioate modification, and "f" represents fluoro modification.

In some embodiments, the anti-sense RNA strand may include a modified RNA strand having a nucleotide sequence of SEQ ID NO. 12 or SEQ ID NO. 14, in which "m" represents O-methyl modification, "s" represents phosphorothioate modification, and "f" represents fluoro modification.

In some embodiments, the siRNA may include a double-stranded RNA including a sense RNA strand having 15 to 25 bases of Ugt2b1 mRNA and an anti-sense RNA strand complementary to 15 to 25 bases of Ugt2b1 mRNA.

According to another aspect of the present disclosure, a method of treating a subject suffering from a disease associated with expression of Ugt2b1 gene is provided. The method may include administering to the subject a short interfering RNA (siRNA). The siRNA may include a sense RNA strand and an anti-sense RNA strand. The sense and anti-sense RNA strands may form an RNA duplex. The sense RNA strand or the anti-sense RNA strand may be 15 to 25 nucleotides in length. The sense RNA strand and the anti-sense RNA strand may be 70%-100% complementary.

According to another aspect of the present disclosure, a method of treating a subject suffering from diabetes is provided. The method may include administering to the subject an effective amount of an siRNA. The siRNA may include a sense RNA strand and an anti-sense RNA strand, the sense and anti-sense RNA strands forming an RNA duplex. The sense RNA strand or the anti-sense RNA strand may be 15 to 25 nucleotides in length. The sense RNA strand or the anti-sense RNA strand may be 70%-100% complementary to a part of a nucleotide sequence of Ugt2b1 gene.

According to another aspect of the present disclosure, a short interfering RNA (siRNA) molecule is provided. The siRNA molecule may include a sense RNA strand and an anti-sense RNA strand. The sense and anti-sense RNA strands may form an RNA duplex. The sense RNA strand or the anti-sense RNA strand may be 15 to 25 nucleotides in length. The sense RNA strand or the anti-sense RNA strand may be 70%-100% complementary to a part of a nucleotide sequence of Ugt2b1 gene.

According to another aspect of the present disclosure, an inhibitory RNA for inhibiting the expression of Ugt2b1 gene is provided. The inhibitory RNA may include a double-stranded RNA including a sense RNA strand having 15 to 25 bases of Ugt2b1 mRNA and an anti-sense RNA strand complementary to 15 to 25 bases of Ugt2b1 mRNA.

According to another aspect of the present disclosure, a medical composition is provided. The medical composition may include a short interfering RNA (siRNA) molecule comprising a sense RNA strand and an anti-sense RNA strand. The sense and anti-sense RNA strands may form an RNA duplex. The sense RNA strand or the anti-sense RNA strand may be 15 to 25 nucleotides in length. The sense RNA strand or the anti-sense RNA strand may be 70%-100% complementary to a part of a nucleotide sequence of Ugt2b1 gene. The siRNA may be configured to reduce an expression of the Ugt2b1 gene.

The sense RNA strand and the anti-sense RNA strand may form a hairpin structure.

According to another aspect of the present disclosure, the use of a composition including a short interfering RNA (siRNA) molecule in a preparation of drugs for treating a subject suffering from diabetes is provided. The siRNA may be configured to reduce uridine 5'-diphospho-glucuronosyltransferase (UGT) levels in the subject.

According to another aspect of the present disclosure, the use of a short interfering RNA (siRNA) that inhibits an expression of Ugt2b1 gene in a preparation of drugs for treating a subject suffering from diabetes is provided. The siRNA may include a sense RNA strand and an anti-sense RNA strand. The sense and anti-sense RNA strands may form an RNA duplex. The sense RNA strand or the anti-sense RNA strand may be 15 to 25 nucleotides in length. The sense RNA strand and the anti-sense RNA strand may be 70%-100% complementary.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities, and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. It should be noted that the drawings are not to scale. These embodiments are non-limiting exemplary embodiments, in which like reference numerals represent similar structures throughout the several views of the drawings, and wherein.

DETAILED DESCRIPTION

Figure 1:
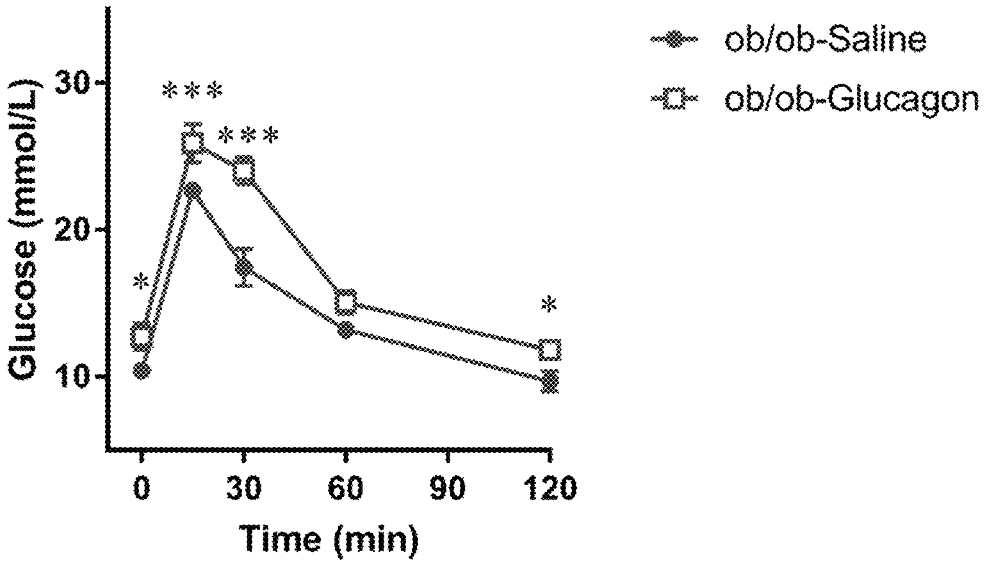
FIG. 1 is an analytical diagram illustrating blood glucose levels tested in GTT in ob/ob mice according to some embodiments of the present disclosure.

The following description is presented to enable any person skilled in the art to make and use the present disclosure and is provided in the context of a particular application and its requirements. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown but is to be accorded the widest scope consistent with the claims.

The terminology used herein is to describe particular example embodiments only and is not intended to be limiting. As used herein, the singular forms "a," "an," and "the" may be intended to include the plural forms as well, unless the context clearly indicates otherwise. It will be further understood that the terms "comprises," "comprising," "includes," and/or "including" when used in this specification, specify the presence of stated features, integers, steps, operations, elements, and/or components, but do not preclude the presence or addition of one or more other features, integers, steps, operations, elements, components, and/or groups thereof.

These and other features, and characteristics of the present disclosure, as well as the methods of operation and functions of the related elements of structure and the combination of parts and economies of manufacture, may become more apparent upon consideration of the following description with reference to the accompanying drawing(s), all of which form a part of this specification. It is to be expressly understood, however, that the drawing(s) is for the purpose of illustration and description only and are not intended to limit the scope of the present disclosure. It is understood that the drawings are not to scale.

The present disclosure provides a method of treating a subject suffering from diabetes. The method may include administering a medical composition including an agent to the subject. The agent may be configured to reduce UGT levels by inhibiting an expression of Ugt2b1 gene. The agent may be an inhibitory RNA (e.g., an siRNA). The siRNA may be used to silent the Ugt2b1 gene, thereby inhibiting the expression of Ugt2b1 gene and further reducing the UGT levels. A decreased or silent expression of the Ugt2b1 gene may decrease blood glucose, thereby treating the subject suffering from diabetes, particularly type II diabetes. The siRNA and the medical composition including the siRNA are also provided. Thus, by using the medical composition including the siRNA which can effectively inhibit the expression of Ugt2b1 gene, the subject suffering from diabetes can be treated with less side effect and reduced economic burden. Compared with traditional drugs, siRNA drugs have many advantages including having more selectable targets, being easier to prepare, having high biological specificity, and maintaining the drug effect for a long time, uneasy to develop drug resistance, etc. In some embodiments, the siRNA may be also used to treat a subject having a disease associated with expression of Ugt2b1 gene. The disease associated with expression of Ugt2b1 gene may include, for example, diabetes, conditions associated with high fat diet, liver neoplasms, fatty liver, hypertrophy, cholestasis, fibrosis, drug-induced liver injury, etc.

As used herein, the term "small interfering RNA (siRNA)" (also known as short interfering RNA or silencing RNA) refers to a class of double-stranded RNA and/or non-coding RNA molecules. siRNA drugs may be used for inducing silencing of protein-coding genes. The siRNA may be used to target mRNA of a specific gene to produce a gene silencing effect. For example, the siRNA may interfere with the expression of specific genes with complementary nucleotide sequences by degrading mRNA after transcription, and preventing translation.

As used herein, the term "subject" of the present disclosure refers to an organism to which the siRNA or a medical composition including the siRNA of the present disclosure may be administered. The subject may include any human or non-human animal, organs, tissue, or cells from any human or non-human animal, or the like, or any combination thereof. Exemplary non-human animal may include Mammalia (such as chimpanzees and other apes and monkey species, or the like), farm animals (such as cattle, sheep, pigs, goats, and horses, or the like), domestic mammals (such as dogs and cats, or the like), laboratory animals (such as mice, rats, and guinea pigs, or the like), etc. In some embodiments, the subject may be cells from a laboratory animal (e.g., mice). For example, the subject may be liver cancer cells from mice (e.g., hepa1-6). In some embodiments, the subject may suffer from one or more diseases (e.g., diabetes, conditions associated with high fat diet, liver neoplasms, fatty liver, hypertrophy, cholestasis, fibrosis, drug-induced liver injury, etc.). For example, the subject may be mice suffering from type II diabetes (e.g., ob/ob mice, db/db mice). The ob/ob mice and the db/db mice are animal models of type II diabetes. The ob/ob mice or obese mice are mutant mice that eat excessively due to mutations in the gene responsible for the production of leptin and becomes profoundly obese. The db/db mice are a genetically mutated mice in which leptin receptors do not function properly. The db/db mice are extremely obese and may have many of the metabolic defects (e.g., hyperphagia, hyperglycemia, hyperinsulinemia, and infertility) that are found in the ob/ob mice.

According to an aspect of the present disclosure, a method of treating a subject suffering from diabetes is provided. The method may include administering a medical composition including an agent to the subject.

The agent of the medical composition may play an important role in treating diabetes. The agent may be configured to reduce uridine 5'-diphospho-glucuronosyltransferase (UGT) levels in the subject to mitigate or treat diabetes. UGT levels herein refer to UGT protein expression levels, and/or UGT enzyme activity levels, or RNA expression levels of genes encoding UGT. In some embodiments, the agent may be configured to reduce UGT levels by inhibiting protein expression of UGT. The protein expression levels or protein activity levels of UGT or RNA expression levels of genes encoding UGT levels may be measured in accordance with conventional processes. For example, RNA expression levels may be measured by northern hybridization, RT-PCR, etc. As another example, protein expression levels may be measured by western blotting, ELISA, etc.

In some embodiments, the agent may be configured to reduce UGT levels by inhibiting expression of genes encoding UGT. The genes encoding UGT may be different for different subjects. For mice with high homology with humans, UGT may mainly include a UGT 1A family and a UGT 2 family. The UGT 2 family may include a UGT 2A family and a UGT 2B family. The genes encoding UGT may include genes encoding UGT 1A family, genes encoding UGT 2A family, and genes encoding UGT 2B family. Exemplary genes encoding UGT 1A family may include Ugt1a1 gene. Exemplary genes encoding UGT 2A family may include Ugt2a1 gene, Ugt2a2 gene, and Ugt2a3 gene. Exemplary genes encoding UGT 2B family may include Ugt2b1 gene, Ugt2b5 gene, Ugt2b34 gene, Ugt2b35 gene, Ugt2b36 gene, Ugt2b37 gene, and Ugt2b38 gene. For humans, UGT may include a UGT1A family, a UGT2 family, a UGT3 family, and a UGT8 family. The UGT 2 family may include a UGT 2A family and a UGT 2B family. The genes encoding UGT may include genes encoding UGT 1A family, genes encoding UGT 2A family, genes encoding UGT 2B family, genes encoding UGT3 family, and genes encoding UGT 8 family. Exemplary genes encoding UGT 1A family may include Ugt1a1 gene, Ugt1a3 gene, Ugt1a4 gene, Ugt1a5 gene, Ugt1a6 gene, Ugt1a7 gene, Ugt1a8 gene, Ugt1a9 gene, and Ugt1a10 gene. Exemplary genes encoding UGT 2A family may include Ugt2a1 gene, Ugt2a2 gene, and Ugt2a3 gene. Exemplary genes encoding UGT 2B family may include Ugt2b4 gene, Ugt2b7 gene, Ugt2b10 gene, Ugt2b11 gene, Ugt2b15 gene, Ugt2b17 gene, and Ugt2b28 gene. Exemplary genes encoding UGT3 family may include Ugt3a1 gene and Ugt3a2 gene. Exemplary genes encoding UGT8 family may include Ugt8a1 gene. In some embodiments, the agent may be configured to reduce UGT levels by inhibiting an expression of at least one of genes encoding UGT 2B family. In some embodiments, the agent may be configured to reduce UGT levels by inhibiting an expression of the Ugt2b1 gene. In some embodiments, the agent may be configured to reduce UGT levels by inhibiting expressions of a plurality of genes encoding UGT, such as the Ugt2b1 gene and one or more other genes (e.g., the Ugt2a1 gene, the Ugt2b8 gene).

The expression level of the Ugt2b1 gene may be associated with diabetes, particularly type II diabetes caused by, for example, obesity or overweight. The Ugt2b1 gene may participate in a glucagon signaling pathway. The glucagon, working to raise the concentration of glucose, may be in positive correlation with the glucagon receptor (GCGR), e.g., the glucagon may facilitate production of GCGR. Further, the GCGR may facilitate the expression of the Ugt2b1 gene by the constitutive androstane receptor (CAR) and the pregnane X receptor (PXR). Thus, the expression of the Ugt2b1 gene may be in positive correlation with glucose. That is, upregulated expression of the Ugt2b1 gene may increase the blood glucose while downregulated expression of the Ugt2b1 gene may decrease the blood glucose (see Examples 1 and 2 described hereinafter). Thus, the Ugt2b1 gene may be considered as one of the causes of diabetes and may be selected as a target for siRNA treatment.

In some embodiments, the agent may include one or more small molecules or protein-based agents (such as an antibody) to block protein expression of UGT or reduce protein activity of UGT. For example, the small molecules may include desloratadine, lapatinib, pazopanib, regorafenib, sorafenib, etc. The protein-based agents may include an anti-UGT2B7 antibody, an anti-UGT2B10 antibody, an anti-UGT2B15 antibody, etc.

In some embodiments, the agent may be or include an inhibitory RNA. The inhibitory RNA may be an engineered RNA molecule configured to inhibit gene expression. The inhibitory RNA may be used to reduce UGT levels, for example, by inhibiting an expression of a gene encoding UGT, such as the Ugt2b1 gene. The inhibitory RNA may include a microRNA (miRNA), an siRNA, and a short hairpin RNA (shRNA). In some embodiments, the inhibitory RNA may be an miRNA. The miRNA may be used to inhibit the expression of a plurality of target genes, such as the Ugt2b1 gene and one or more other genes (e.g., the Ugt2a1 gene, the Ugt2b8 gene). In some embodiments, the inhibitory RNA may be an siRNA. The siRNA may be used to target only one specific gene, for example, the Ugt2b1 gene to silence it (e.g., downregulate its expression).

siRNAs and miRNAs may downregulate the expression of one or more genes encoding UGT and/or their mRNA transcripts. The discovery of siRNA and miRNA opens up a whole new therapeutic approach for the treatment of diseases by targeting genes (e.g., the Ugt2b1 gene) that are involved causally in pathological processes of, e.g., diabetes. In some embodiments, the siRNA may be used to treat a subject having a disease associated with expression of Ugt2b1 gene. The disease associated with expression of Ugt2b1 gene may include, for example, diabetes, conditions associated with high fat diet, liver neoplasms, fatty liver, hypertrophy, cholestasis, fibrosis, drug-induced liver injury, etc.

The siRNA may include a sense RNA strand and an anti-sense RNA strand. The sense and the anti-sense RNA strands may form an RNA duplex with two nucleotides overhang at 3' end on each strand. The sense RNA strand may be a strand the same as part of an mRNA sequence of a target gene (e.g., the Ugt2b1 gene). The anti-sense RNA strand may be a strand complementary to the part of the mRNA sequence of the target gene (e.g., the Ugt2b1 gene). The anti-sense RNA strand may be configured to identify the mRNA of the target gene and then bind thereto for initiating transcriptional silencing.

In some embodiments, the sense RNA strand or the anti-sense RNA strand may include or not include one or more nucleotides overhang at 3' end (also referred to as an overhang) in length. The overhang herein may be configured to increase the stability of exogenous siRNA in a subject, confer increased nuclease resistance, and/or reduce cost. Exemplary overhangs may include one nucleotide, two nucleotides, three nucleotides, etc., which are not limited herein. In some embodiments, there may be two overhangs at 3' end of one strand of an siRNA. Overhangs may be a default option (e.g., UU or dTdT) for siRNA design or complementary to a part of mRNA sequence of the target gene. In some embodiments, the sense RNA strand may not include two nucleotides overhang at 3' end in length while the anti-sense RNA strand may include two nucleotides overhang at 3' end in length. In some embodiments, the sense RNA strand may include two nucleotides overhang at 3' end in length while the anti-sense RNA strand may not include two nucleotides overhang at 3' end in length. In some embodiments, the two nucleotides overhang at 3' end of the sense RNA strand may be, for example, UU or dTdT The nucleotides (e.g., two nucleotides) overhang at 3' end of the anti-sense RNA strand may be prescribed (for example, UU or dTdT) or complementary to a part of nucleotide sequence of the mRNA of the target gene (e.g., GC, UC, CA, AC, AA). In some embodiments, the sense RNA strand and the anti-sense RNA strand may each include two nucleotides overhang at 3' end in length. In some embodiments, the sense RNA strand and the anti-sense RNA strand may each not include two nucleotides overhang at 3' end in length. It should be noted that the sense RNA strand and/or the anti-sense RNA strand with or without overhangs are all within the protection scope of the present disclosure. In some embodiments, the sense RNA strand and the anti-sense RNA strand may form a hairpin structure to improve the stability of the siRNA and/or enhance the functional performance of the siRNA. For example, the sense RNA strand and the anti-sense RNA strand may be joined by a loop to form a hairpin structure.

In some embodiments, the sense RNA strand or the anti-sense RNA strand may be 15 to 27 nucleotides in length (not including overhangs). In some embodiments, the sense RNA strand or the anti-sense RNA strand may be 15 to 25 nucleotides in length (not including overhangs). In some embodiments, the sense RNA strand or the anti-sense RNA strand may be 19 to 23 nucleotides in length (not including overhangs). In some embodiments, the sense RNA strand or the anti-sense RNA strand may be 19 to 21 nucleotides in length (not including overhangs). In some embodiments, the sense RNA strand may be 19 nucleotides in length (not including overhangs). In some embodiments, the anti-sense RNA strand may be 21 nucleotides in length (not including overhangs).

The sense RNA strand and the anti-sense RNA strand may be 70%-100% complementary. A complementary percentage herein refers to a percentage of a complementary length of a sense RNA strand and an anti-sense RNA strand to a longer length of the two. In some embodiments, the sense RNA strand and the anti-sense RNA strand may be 75%-100% complementary, 80%-100% complementary, 85%-100% complementary, 90%-100% complementary, etc. In some embodiments, the sense RNA strand and the anti-sense RNA strand may be 90%-100% complementary. In some embodiments, the complementary percentage may be associated with lengths of the sense RNA strand and the anti-sense RNA strand. The sense RNA strand and the anti-sense RNA strand may be greater than 90% complementary, e.g., 90.47% complementary when the sense RNA strand is 19 nucleotides in length and the anti-sense RNA strand is 21 nucleotides in length.

In some embodiments, the sense RNA strand may have a nucleotide sequence having 70% or more (e.g., 75%, 80%, 85%, 87%, 90%, 92%, 95%, 97%, or 99%, or the like) similarity with SEQ ID NO. 1. In some embodiments, the anti-sense RNA strand may have a nucleotide sequence having 70% or more (e.g., 75%, 80%, 85%, 87%, 90%, 92%, 95%, 97%, or 99%, or the like) similarity with SEQ ID NO. 2. In some embodiments, the sense RNA strand may have a nucleotide sequence having at least 80% similarity with SEQ ID NO. 1, and the anti-sense RNA strand may have a nucleotide sequence having at least 80% similarity with SEQ ID NO. 2. In some embodiments, the sense RNA strand may have a nucleotide sequence having at least 90% similarity with SEQ ID NO. 1, and the anti-sense RNA strand may have a nucleotide sequence having at least 90% similarity with SEQ ID NO. 2. In some embodiments, the sense RNA strand may have a nucleotide sequence having at least 95% similarity with SEQ ID NO. 1, and the anti-sense RNA strand may have a nucleotide sequence having at least 95% similarity with SEQ ID NO. 2. In some embodiments, the sense RNA strand may have a nucleotide sequence of SEQ ID NO. 1, and the anti-sense RNA strand may have a nucleotide sequence of SEQ ID NO. 2.

In some embodiments, the sense RNA strand may have a nucleotide sequence having 70% or more (e.g., 75%, 80%, 85%, 87%, 90%, 92%, 95%, 97%, or 99%, or the like) similarity with SEQ ID NO. 3. In some embodiments, the anti-sense RNA strand may have a nucleotide sequence having 70% or more (e.g., 75%, 80%, 85%, 87%, 90%, 92%, 95%, 97%, or 99%, or the like) similarity with SEQ ID NO. 4. In some embodiments, the sense RNA strand may have a nucleotide sequence having at least 80% similarity with SEQ ID NO. 3, and the anti-sense RNA strand may have a nucleotide sequence having at least 80% similarity with SEQ ID NO. 4. In some embodiments, the sense RNA strand may have a nucleotide sequence having at least 90% similarity with SEQ ID NO. 3, and the anti-sense RNA strand may have a nucleotide sequence having at least 90% similarity with SEQ ID NO. 4. In some embodiments, the sense RNA strand may have a nucleotide sequence having at least 95% similarity with SEQ ID NO. 3, and the anti-sense RNA strand may have a nucleotide sequence having at least 95% similarity with SEQ ID NO. 4. In some embodiments, the sense RNA strand may have a nucleotide sequence of SEQ ID NO. 3, and the anti-sense RNA strand may have a nucleotide sequence of SEQ ID NO. 4.

In some embodiments, the sense RNA strand may have a nucleotide sequence having 70% or more (e.g., 75%, 80%, 85%, 87%, 90%, 92%, 95%, 97%, or 99%, or the like) similarity with SEQ ID NO. 5. In some embodiments, the anti-sense RNA strand may have a nucleotide sequence having 70% or more (e.g., 75%, 80%, 85%, 87%, 90%, 92%, 95%, 97%, or 99%, or the like) similarity with SEQ ID NO. 6. In some embodiments, the sense RNA strand may have a nucleotide sequence having at least 80% similarity with SEQ ID NO. 5, and the anti-sense RNA strand may have a nucleotide sequence having at least 80% similarity with SEQ ID NO. 6. In some embodiments, the sense RNA strand may have a nucleotide sequence having at least 90% similarity with SEQ ID NO. 5, and the anti-sense RNA strand may have a nucleotide sequence having at least 90% similarity with SEQ ID NO. 6. In some embodiments, the sense RNA strand may have a nucleotide sequence having at least 95% similarity with SEQ ID NO. 5, and the anti-sense RNA strand may have a nucleotide sequence having at least 95% similarity with SEQ ID NO. 6. In some embodiments, the sense RNA strand may have a nucleotide sequence of SEQ ID NO. 5, and the anti-sense RNA strand may have a nucleotide sequence of SEQ ID NO. 6.

In some embodiments, the sense RNA strand may have a nucleotide sequence having 70% or more (e.g., 75%, 80%, 85%, 87%, 90%, 92%, 95%, 97%, or 99%, or the like) similarity with SEQ ID NO. 7. In some embodiments, the anti-sense RNA strand may have a nucleotide sequence having 70% or more (e.g., 75%, 80%, 85%, 87%, 90%, 92%, 95%, 97%, or 99%, or the like) similarity with SEQ ID NO. 8. In some embodiments, the sense RNA strand may have a nucleotide sequence having at least 80% similarity with SEQ ID NO. 7, and the anti-sense RNA strand may have a nucleotide sequence having at least 80% similarity with SEQ ID NO. 8. In some embodiments, the sense RNA strand may have a nucleotide sequence having at least 90% similarity with SEQ ID NO. 7, and the anti-sense RNA strand may have a nucleotide sequence having at least 90% similarity with SEQ ID NO. 8. In some embodiments, the sense RNA strand may have a nucleotide sequence having at least 95% similarity with SEQ ID NO. 7, and the anti-sense RNA strand may have a nucleotide sequence having at least 95% similarity with SEQ ID NO. 8. In some embodiments, the sense RNA strand may have a nucleotide sequence of SEQ ID NO. 7, and the anti-sense RNA strand may have a nucleotide sequence of SEQ ID NO. 8.

In some embodiments, the sense RNA strand may have a nucleotide sequence having 70% or more (e.g., 75%, 80%, 85%, 87%, 90%, 92%, 95%, 97%, or 99%, or the like) similarity with SEQ ID NO. 9. In some embodiments, the anti-sense RNA strand may have a nucleotide sequence having 70% or more (e.g., 75%, 80%, 85%, 87%, 90%, 92%, 95%, 97%, or 99%, or the like) similarity with SEQ ID NO. 10. In some embodiments, the sense RNA strand may have a nucleotide sequence having at least 80% similarity with SEQ ID NO. 9, and the anti-sense RNA strand may have a nucleotide sequence having at least 80% similarity with SEQ ID NO. 10. In some embodiments, the sense RNA strand may have a nucleotide sequence having at least 90% similarity with SEQ ID NO. 9, and the anti-sense RNA strand may have a nucleotide sequence having at least 90% similarity with SEQ ID NO. 10. In some embodiments, the sense RNA strand may have a nucleotide sequence having at least 95% similarity with SEQ ID NO. 9, and the anti-sense RNA strand may have a nucleotide sequence having at least 95% similarity with SEQ ID NO. 10. In some embodiments, the sense RNA strand may have a nucleotide sequence of SEQ ID NO. 9, and the anti-sense RNA strand may have a nucleotide sequence of SEQ ID NO. 10.

In some embodiments, the siRNA may include a double-stranded RNA including a sense RNA strand having 248 to 266, 1019 to 1037, 1253 to 1271, 1864 to 1882, and/or 2082 to 2100 bases of Ugt2b1 mRNA and an anti-sense RNA strand complementary to 246 to 266 (or 248 to 266), 1017 to 1037 (or 1019 to 1037), 1251 to 1271 (or 1253 to 1271), 1862 to 1882 (or 1864 to 1882), and/or 2080 to 2100 (or 2082 to 2100) bases of Ugt2b1 mRNA. In some embodiments, the siRNA may include a double-stranded RNA including a sense RNA strand having 1253 to 1271, 1864 to 1882, and/or 2082 to 2100 bases of Ugt2b1 mRNA and an anti-sense RNA strand complementary to 1251 to 1271 (or 1253 to 1271), 1862 to 1882 (or 1864 to 1882), and/or 2080 to 2100 (or 2082 to 2100) bases of Ugt2b1 mRNA. In some embodiments, the siRNA may be a double-stranded RNA including a sense RNA strand having 1253 to 1271 and/or 1864 to 1882 bases of Ugt2b1 mRNA and an anti-sense RNA strand complementary to 1251 to 1271 (or 1253 to 1271) and/or 1862 to 1882 (1864 to 1882) bases of Ugt2b1 mRNA. The sequence of the Ugt2b1 mRNA may be listed as SEQ ID NO. 27.

For illustration purposes, an siRNA including a double-stranded RNA including a sense RNA strand having 248 to 266 bases of Ugt2b1 mRNA and an anti-sense RNA strand complementary to 246 to 266 (or 248 to 266) bases of Ugt2b1 mRNA may be referred to as a first siRNA; an siRNA including a double-stranded RNA including a sense RNA strand having 1019 to 1037 bases of Ugt2b1 mRNA and an anti-sense RNA strand complementary to 1017 to 1037 (or 1019 to 1037) bases of Ugt2b1 mRNA may be referred to as a second siRNA; an siRNA including a double-stranded RNA including a sense RNA strand having 1253 to 1271 bases of Ugt2b1 mRNA and an anti-sense RNA strand complementary to 1251 to 1271 (or 1253 to 1271) bases of Ugt2b1 mRNA may be referred to as a third siRNA; an siRNA including a double-stranded RNA including a sense RNA strand having 1864 to 1882 bases of Ugt2b1 mRNA and an anti-sense RNA strand complementary to 1862 to 1882 (or 1864 to 1882) bases of Ugt2b1 mRNA may be referred to as a fourth siRNA; an siRNA including a double-stranded RNA including a sense RNA strand having 2082 to 2100 bases of Ugt2b1 mRNA and an anti-sense RNA strand complementary to 2080 to 2100 (or 2082 to 2100) bases of Ugt2b1 mRNA may be referred to as a fifth siRNA.

In some embodiments, a silencing efficiency of the siRNA to reduce or inhibit an expression of the Ugt2b1 gene may vary depending on the region of the mRNA of the target gene (e.g., the Ugt2b1 gene) to which the siRNA is complementary. A silencing efficiency of an siRNA herein refers to a ratio of an mRNA level of the gene silenced by the siRNA compared to an mRNA level of a reference gene (e.g., 36B4 gene). The mRNA levels may be determined by, for example, RT-PCR. The silencing efficiency may be expressed by, for example, a percentage. In some embodiments, the silencing efficiency of the siRNA (e.g., the first siRNA, the second siRNA, the third siRNA, the fourth siRNA, and/or the fifth siRNA) may be greater than or equal to 25%. In some embodiments, silencing efficiencies of at least four of the above siRNAs (e.g., the second siRNA, the third siRNA, the fourth siRNA, the fifth siRNA) may be greater than or equal to 40%. In some embodiments, silencing efficiencies of at least four of the above siRNAs (e.g., the second siRNA, the third siRNA, the fourth siRNA, the fifth siRNA) may be greater than or equal to 50%. In some embodiments, silencing efficiencies of at least three of the above siRNAs (e.g., the second siRNA, the third siRNA, the fourth siRNA) may be greater than or equal to 60%. In some embodiments, silencing efficiencies of at least two of the above siRNAs (e.g., the third siRNA, the fourth siRNA) may be greater than or equal to 75%. In some embodiments, a silencing efficiency of at least one of the above siRNAs (e.g., the fourth siRNA) may be greater than or equal to 85%.

It should be noted that the siRNA(s) for targeting the Ugt2b1 gene may be designed by using various strategies (e.g., manipulating G/C content, avoiding U-rich sequences, preventing siRNA sequences homologous to other genes, etc.) for those skilled to the art, and the sequences of siRNA(s) described above are not intended to be limiting.

In some embodiments, one or more nucleotides of the siRNA(s) may be modified chemically to form modified nucleotide(s). Chemical modification of the nucleotide(s) of the siRNA may increase stability and/or specificity of the siRNA, minimize immunogenicity of the siRNA, and reduce off-target effect of the siRNA. The modified nucleotide(s) of the siRNA may be used to prepare the medical composition for treating diabetes or a medical composition for reducing or inhibiting the expression of the Ugt2b1 gene. Exemplary chemical modifications that are commonly used in siRNA may include a ribose 2'-OH group modification, locked nucleic acid (LNA) and unlocked nucleic acid (UNA) modifications, a backbone modification, etc. The ribose 2'-OH group modification may involve the substitution of the ribose 2'-OH group with other chemical groups, including 2'-O-methyl (2'-O-Me), 2'-fluoro (2'-F), and 2'-methoxyethyl (2'-O-MOE). In the LNA modification, a ribose may be locked in a C3' endo conformation by introducing a 2'-O and 4'-C methylene bridge. In the UNA modification, a ribose ring may be cleaved between 2'-C and 3'-C. The backbone modification may involve substituting the phosphodiester backbone linkage, and include a phosphorothioate modification or a boranophosphate modification. A nonbridging phosphate atom may be replaced with a sulfur atom to give a phosphorothioate modification, or replaced with a borane ($BH_3$) moiety to give a boranophosphate modification.

In some embodiments, different strategies of using these chemical modifications may be applied. For example, two or more chemical modifications may be used in combination (e.g., two or more chemical modifications may be performed on an individual nucleotide). As another example, one or more the chemical modifications (e.g., the ribose 2'-OH group modification) may be used together with the phosphorothioate modification. As a further example, only one chemical modification may be used. Correspondingly, in some embodiments, the modified nucleotides of the siRNA may include an O-methyl modified nucleotide, a fluoro modified nucleotide, an O-MOE modified nucleotide, a phosphorothioate or boranophosphate modified nucleotide, an LNA modified nucleotide, an UNA modified nucleotide, or the like, or any combination thereof. In some embodiments, the modified nucleotides of the siRNA may include an O-methyl modified nucleotide, a fluoro modified nucleotide, an O-MOE modified nucleotide, a phosphorothioate modified nucleotide, or the like, or any combination thereof. In some embodiments, the modified nucleotides of the siRNA may include an O-methyl modified nucleotide, a fluoro modified nucleotide, a phosphorothioate modified nucleotide, or the like, or any combination thereof.

For brevity, the O-methyl modified nucleotide may be represented by a letter of "m", the phosphorothioate modified nucleotide may be represented by a letter of "s", and the fluoro modified nucleotide may be represented by a letter of "f". Merely by way of example, the modified nucleotides of the siRNA may include an O-methyl modified guanine (i.e., Gm), an O-methyl modified cytosine (i.e., Cm), an O-methyl modified adenine (i.e., Am), and/or an O-methyl modified uracil (i.e., Um). As another example, the modified nucleotides of the siRNA may include a phosphorothioate modified guanine (i.e., Gs), a phosphorothioate modified cytosine (i.e., Cs), a phosphorothioate modified adenine (i.e., As), and/or a phosphorothioate modified uracil (i.e., Us). As still another example, the modified nucleotides of the siRNA may include a fluoro modified guanine (i.e., Gf), a fluoro modified cytosine (i.e., Cf), a fluoro modified adenine (i.e., Af), and/or a fluoro modified uracil (i.e., Uf). As a further example, the modified nucleotides of the siRNA may include an O-methyl and phosphorothioate modified guanine (i.e., Gms), an O-methyl and phosphorothioate modified cytosine (i.e., Cms), an O-methyl and phosphorothioate modified adenine (i.e., Ams), and/or an O-methyl and phosphorothioate modified uracil (i.e., Ums). As still a further example, the modified nucleotides of the siRNA may include a fluoro and phosphorothioate modified guanine (i.e., Gfs), a fluoro and phosphorothioate modified cytosine (i.e., Cfs), a fluoro and phosphorothioate modified adenine (i.e., Afs), and/or a fluoro and phosphorothioate modified uracil (i.e., Ufs).

In some embodiments, only nucleotides of the sense RNA strand may be modified. In some embodiments, the sense RNA strand may include modified nucleotides at about 25%-100% of nucleotide positions. In some embodiments, the sense RNA strand may include modified nucleotides at about 60%-100% of nucleotide positions. In some embodiments, the sense RNA strand may include modified nucleotides at about 80%-100% of nucleotide positions. In some embodiments, the sense RNA strand may include modified nucleotides at about 90%-100% of nucleotide positions. In some embodiments, the sense RNA strand may include modified nucleotides at 100% of nucleotide positions. In some embodiments, the siRNA may include a modified sense RNA strand having a nucleotide sequence having 70% or more (e.g., 75%, 80%, 85%, 90%, 95%, or 99%, or the like) similarity with SEQ ID NO. 11 (or SEQ ID NOs. 13, 15, 17, or 19), and an unmodified anti-sense RNA strand having a nucleotide sequence having 70% or more (e.g., 75%, 80%, 85%, 90%, 95%, or 99%, or the like) similarity with SEQ ID NO. 2 (or SEQ ID NOs. 4, 6, 8, or 10), respectively. In some embodiments, the siRNA may include a modified sense RNA strand having a nucleotide sequence having at least 90% similarity with SEQ ID NO. 11 (or SEQ ID NOs. 13, 15, 17, or 19), and an unmodified anti-sense RNA strand having a nucleotide sequence having at least 90% similarity with SEQ ID NO. 2 (or SEQ ID NOs. 4, 6, 8, or 10), respectively. In some embodiments, the siRNA may include a modified sense RNA strand having a nucleotide sequence as indicated by SEQ ID NO. 11 (or SEQ ID NOs. 13, 15, 17, or 19), and an unmodified anti-sense RNA strand having a nucleotide sequence as indicated by SEQ ID NO. 2 (or SEQ ID NOs. 4, 6, 8, or 10), respectively.

In some embodiments, only nucleotides of the anti-sense RNA strand may be modified. In some embodiments, the anti-sense RNA strand may include modified nucleotides at about 25%-100% of nucleotide positions. In some embodiments, the anti-sense RNA strand may include modified nucleotides at about 60%-100% of nucleotide positions. In some embodiments, the anti-sense RNA strand may include modified nucleotides at about 80%-100% of nucleotide positions. In some embodiments, the anti-sense RNA strand may include modified nucleotides at about 90%-100% of nucleotide positions. In some embodiments, the anti-sense RNA strand may include modified nucleotides at 100% of nucleotide positions. In some embodiments, the siRNA may include an unmodified sense RNA strand having a nucleotide sequence having 70% or more (e.g., 75%, 80%, 85%, 90%, 95%, or 99%, or the like) similarity with SEQ ID NO. 1 (or SEQ ID NOs. 3, 5, 7, or 9), and a modified anti-sense RNA strand having a nucleotide sequence having 70% or more (e.g., 75%, 80%, 85%, 90%, 95%, or 99%, or the like) similarity with SEQ ID NO. 12 (or SEQ ID NOs. 14, 16, 18, or 20), respectively. In some embodiments, the siRNA may include an unmodified sense RNA strand having a nucleotide sequence having at least 90% similarity with SEQ ID NO. 1 (or SEQ ID NOs. 3, 5, 7, or 9), and a modified anti-sense RNA strand having a nucleotide sequence having at least 90% similarity with SEQ ID NO. 12 (or SEQ ID NOs. 14, 16, 18, or 20), respectively. In some embodiments, the siRNA may include an unmodified sense RNA strand having a nucleotide sequence as indicated by SEQ ID NO. 1 (or SEQ ID NOs. 3, 5, 7, or 9), and a modified anti-sense RNA strand having a nucleotide sequence as indicated by SEQ ID NO. 12 (or SEQ ID NOs. 14, 16, 18, or 20), respectively.

In some embodiments, nucleotides of both the sense RNA strand and the anti-sense RNA strand may be modified. In some embodiments, the sense RNA strand and the anti-sense RNA strand may include modified nucleotides at about 25%-100% of nucleotide positions. In some embodiments, the sense RNA strand and the anti-sense RNA strand may include modified nucleotides at about 60%-100% of nucleotide positions. In some embodiments, the sense RNA strand and the anti-sense RNA strand may include modified nucleotides at about 80%-100% of nucleotide positions. The sense RNA strand and the anti-sense RNA strand may include modified nucleotides at about 90%-100% of nucleotide positions. In some embodiments, the sense RNA strand and the anti-sense RNA strand may include modified nucleotides at 100% of nucleotide positions. The sense RNA strand may include a modified RNA strand having a nucleotide sequence having 70% or more (e.g., 75%, 80%, 85%, 90%, 95%, or 99%, or the like) similarity with SEQ ID NO. 11 (or SEQ ID NOs. 13, 15, 17, or 19), and the anti-sense RNA strand may include a modified RNA strand having a nucleotide sequence having 70% or more (e.g., 75%, 80%, 85%, 90%, 95%, or 99%, or the like) similarity with SEQ ID NO. 12 (or SEQ ID NOs. 14, 16, 18, or 20), respectively. The sense RNA strand may include a modified RNA strand having a nucleotide sequence having at least 90%, 95%, or 99% similarity with SEQ ID NO. 11 (or SEQ ID NOs. 13, 15, 17, or 19), and the anti-sense RNA strand may include a modified RNA strand having a nucleotide sequence having at least 90%, 95%, or 99% similarity with SEQ ID NO. 12 (or SEQ ID NOs. 14, 16, 18, or 20), respectively. In some embodiments, the sense RNA strand may include a modified RNA strand having a nucleotide sequence as indicated by SEQ ID NO. 11 (or SEQ ID NOs. 13, 15, 17, or 19), and the anti-sense RNA strand may include a modified RNA strand having a nucleotide sequence as indicated by SEQ ID NO. 12 (or SEQ ID NOs. 14, 16, 18, or 20), respectively. In some embodiments, the sense RNA strand may include a modified RNA strand having a nucleotide sequence of SEQ ID NO. 11 or SEQ ID NO. 13. In some embodiments, the anti-sense RNA strand may include a modified RNA strand having a nucleotide sequence of SEQ ID NO. 12 or SEQ ID NO. 14. Merely by way of example, the siRNA may include a modified RNA strand having a nucleotide sequence as indicated by SEQ ID NO. 11, and the anti-sense RNA strand may include a modified RNA strand having a nucleotide sequence as indicated by SEQ ID NO. 12.

In some embodiments, the medical composition may further include a delivery medium. In some embodiments, the delivery medium may be used to facilitate the delivery of the agent into the subject and/or facilitate the uptake of the agent. For example, the delivery medium may be used to deliver the siRNA in the subject for facilitating the cellular uptake of the siRNA to target the Ugt2b1 gene, thereby protecting the nucleotides of the siRNA from premature nuclease degradation, decreasing or preventing potential side effect(s) of the siRNA, and hence enhancing treatment efficiency of disease(s) (e.g., diabetes). Exemplary delivery medium may include a virus vector (e.g., an adenovirus vector, a lentivirus vector, a retrovirus vector), a nonviral vector, etc. The nonviral vector may include a polymer-based vector (e.g., polyethylenimine (PEI), dendrimer, chitosan, atelocollagen, cyclodextrin), a lipid-based vector, or lipolyplexes (e.g., stearic acid-modified PEI, cholesterol and deoxycholic acid-modified PEI) composed of both polymers and lipids in an attempt to address the limitations of polymer-based and lipid-based vectors by combining the advantageous characteristics of both. Exemplary lipid-based vector may include an ionizable lipid nanoparticle (iLNP) (e.g., LP171 described in Example 4), a cationic lipid, etc. The cationic lipid may be, for example, 1,2-dioleoyloxy-3-trimethylammonium propane (DOTAP) and 1,2-di-O-octadecenyl-3-trimethylammonium propane (DOTMA) which are often used in combination with neutral lipids such as dioleoylphosphatidylethanolamine (DOPE) and cholesterol to enhance transfection efficiency. Many of the commercially available lipid-based vectors may include Lipofectamine, Oligofectamine, DharmaFECT, siPORT, and TransIT-TKO which have been frequently used for RNA delivery. In some embodiments, the delivery medium may include exosomes, polypeptides, carbon nanotubes, nanocarriers (e.g., non-viral nanocarriers, metal nanocarriers), etc. In some embodiments, a virus vector or a nonviral vector may be used to deliver the siRNA. In some embodiments, the lipid-based vector, for example, an LP171 may be used to deliver the siRNA. It should be noted that the above-described delivery mediums are merely provided by way of illustration, and not intended to be limiting.

In some embodiments, the medical composition may include a pharmacologically acceptable carrier including, for example, a diluent (such as water, ethylalcohol, macrogol, propylene glycol, citric acid, acetic acid, phosphoric acid, lactic acid, sodium lactate, sulfuric acid, sodium hydroxide, etc.), a pH adjusting agent or a buffer (such as sodium citrate, sodium acetate, sodium phosphate, etc.), and/or a stabilizer (such as sodium pyrosulfite, ethylenediaminetetraacetic acid, thioglycolic acid, thiolactic acid, monosaccharides, disaccharides, sugar alcohols, amino acids, non-ionic surfactants, human albumin etc.), etc. In some embodiments, the medical composition may further include a sufficient amount of a compound for preparing an isotonic solution (such as salt, glucose, mannitol or glycerin, etc.). In some embodiments, the medical composition may include an adjuvant (e.g., glucose, amino acids, human albumin) for increasing the nutrition and an absorption rate of the medical composition.

The medical composition may be administered in various routes including an oral route or a parenteral route (e.g., injection). The preparation types for oral administration may include, for example, tablets, pills, capsules, powders, granules, syrups, or the like. The preparation types for parenteral administration may include, for example, injections, external preparations, suppositories, etc.

The medical composition may include an effective amount of the siRNA to treat diabetes. The effective amount of the siRNA may be in the range of approximately 0.05 mg/kg/day to 1 mg/kg/day, 0.1 mg/kg/day to 1 mg/kg/day, 0.08 mg/kg/day to 0.8 mg/kg/day, 0.1 mg/kg/day to 0.6 mg/kg/day, 0.12 mg/kg/day to 0.4 mg/kg/day, 0.14 mg/kg/day to 0.35 mg/kg/day, 0.16 mg/kg/day to 0.32 mg/kg/day, 0.18 mg/kg/day to 0.3 mg/kg/day, or 0.2 mg/kg/day to 0.25 mg/kg/day. In some embodiments, the effective amount of the siRNA may be approximately 0.2 mg/kg/day. In some embodiments, the medical composition may be administered to a subject each day, every 2 days, every 3 days, 5 days, a week, etc.

As a dose of administration of the medical composition may vary depending on an active ingredient (e.g., siRNA), an administration route, an age, a body weight, condition, etc., of a subject, it cannot be fixed. Merely by way of illustration, a dose of the medical composition may be in the range of approximately 0.1 mg/kg/day to 2 mg/kg/day, 0.16 mg/kg/day to 1.6 mg/kg/day, 0.2 mg/kg/day to 1.2 mg/kg/day, or 0.24 mg/kg/day to 0.8 mg/kg/day, 0.28 mg/kg/day to 0.7 mg/kg/day, 0.32 mg/kg/day to 0.64 mg/kg/day, 0.36 mg/kg/day to 0.6 mg/kg/day, or 0.4 mg/kg/day to 0.5 mg/kg/day. In some embodiments, the effective amount of the siRNA may be approximately 0.4 mg/kg/day.

According to another aspect of the present disclosure, a method of treating a subject suffering from a disease associated with the expression of Ugt2b1 gene is provided. The method may include administering to the subject a short interfering RNA (siRNA). The siRNA may include a sense RNA strand and an anti-sense RNA strand. The sense and anti-sense RNA strands may form an RNA duplex. The sense RNA strand or the anti-sense RNA strand may be 19 to 21 nucleotides in length. The sense RNA strand and the anti-sense RNA strand may be 70%-100% complementary. More descriptions regarding the siRNA for treating a subject suffering from a disease associated with expression of Ugt2b1 gene can be found elsewhere in the present disclosure, and are not repeated herein.

According to another aspect of the present disclosure, a method of treating a subject suffering from diabetes is provided. The method may include administering to the subject an effective amount of an siRNA. The siRNA may include a sense RNA strand and an anti-sense RNA strand. The sense and anti-sense RNA strands may form an RNA duplex. The sense RNA strand or the anti-sense RNA strand may be 19 to 21 nucleotides in length. The sense RNA strand and the anti-sense RNA strand may be 70%-100% complementary to a part of the nucleotide sequence of Ugt2b1 gene. The effective amount of the siRNA may be in a range of approximately 0.05 mg/kg/day to 1 mg/kg/day, 0.1 mg/kg/day to 1 mg/kg/day, 0.08 mg/kg/day to 0.8 mg/kg/day, 0.1 mg/kg/day to 0.6 mg/kg/day, 0.12 mg/kg/day to 0.4 mg/kg/day, 0.14 mg/kg/day to 0.35 mg/kg/day, 0.16 mg/kg/day to 0.32 mg/kg/day, 0.18 mg/kg/day to 0.3 mg/kg/day, or 0.2 mg/kg/day to 0.25 mg/kg/day. More descriptions regarding the siRNA for treating a subject suffering from a disease associated with expression of Ugt2b1 gene can be found elsewhere in the present disclosure, and are not repeated herein.

According to a further aspect of the present disclosure, a short interfering RNA (siRNA) molecule is provided. The siRNA molecule may include the siRNA and/or the delivery medium described above. Additionally or alternatively, the siRNA molecule may include a pharmacologically acceptable carrier (such as a stabilizer, a buffer, or the like) described above. The siRNA molecule may be introduced into the subject with or without the acceptable carrier via systemic administration and local administration. The systemic administration may include intravenous, intraperitoneal, inhalation, oral administration, etc. The local administration may include subcutaneous injection, intravitreal administration, intrathecal, intrapulmonary, intramuscular administration, etc. The siRNA molecule may be formulated and used as, for example, powders, tablets, capsules or elixirs for oral administration, suppositories for rectal administration, sterile solutions, suspensions for injectable administration, and the other compositions known in the art. In some embodiments, the siRNA molecule may be freeze-dried powder, and may be soluble to a solvent (e.g., water, saline solution) for injectable administration (e.g., intravenous injection).

In some embodiments, the effective amount of the siRNA may be in a range of approximately 0.05 mg/kg/day to 1 mg/kg/day, 0.1 mg/kg/day to 1 mg/kg/day, 0.08 mg/kg/day to 0.8 mg/kg/day, 0.1 mg/kg/day to 0.6 mg/kg/day, 0.12 mg/kg/day to 0.4 mg/kg/day, 0.14 mg/kg/day to 0.35 mg/kg/day, 0.16 mg/kg/day to 0.32 mg/kg/day, 0.18 mg/kg/day to 0.3 mg/kg/day, or 0.2 mg/kg/day to 0.25 mg/kg/day. In some embodiments, the effective amount of the siRNA may be approximately 0.2 mg/kg/day. In some embodiments, the medical composition may be administered to a subject every 3 days, 5 days, a week, etc.

According to a further aspect of the present disclosure, an inhibitory RNA for inhibiting the expression of Ugt2b1 gene is provided. The inhibitory RNA may include an siRNA. The siRNA may include a double-stranded RNA including a sense RNA strand having 15 to 25 bases of Ugt2b1 mRNA and an anti-sense RNA strand complementary to 15 to 25 bases of Ugt2b1 mRNA. More descriptions regarding the inhibitory RNA for inhibiting the expression of Ugt2b1 gene can be found elsewhere in the present disclosure, and are not repeated herein.

According to yet another aspect of the present disclosure, a medical composition including a short interfering RNA (siRNA) molecule is provided. The siRNA may be configured to reduce an expression of the Ugt2b1 gene. More descriptions regarding the medical composition including a short interfering RNA (siRNA) molecule can be found elsewhere in the present disclosure, and are not repeated herein.

According to yet another aspect of the present disclosure, the use of a composition including a short interfering RNA (siRNA) molecule in a preparation of drugs for treating a subject suffering from diabetes is provided. The siRNA may be configured to reduce uridine 5'-diphospho-glucuronosyltransferase (UGT) levels in the subject. More descriptions regarding the composition including the siRNA molecule can be found elsewhere in the present disclosure, and are not repeated herein.

According to yet another aspect of the present disclosure, the use of a short interfering RNA (siRNA) that inhibits an expression of Ugt2b1 gene in a preparation of drugs for treating a subject suffering from diabetes is provided. The siRNA may include a sense RNA strand and an anti-sense RNA strand. The sense and anti-sense RNA strands may form an RNA duplex. The sense RNA strand or the anti-sense RNA strand may be 19 to 21 nucleotides in length; and the sense RNA strand and the anti-sense RNA strand may be 70%-100% complementary. More descriptions regarding the siRNA molecule can be found elsewhere in the present disclosure, and are not repeated herein.

The present disclosure is further described according to the following examples, which should not be construed as limiting the scope of the present disclosure.

TABLE 1

| SEQ ID NO. | Description | Sequence |
|---|---|---|
| SEQ ID NO. 1 | siRNA1864 sense strand | GGUUACUGUAGUUCACAAA |
| SEQ ID NO. 2 | siRNA1864 anti-sense strand | UUUGUGAACUACAGUAACCUC |
| SEQ ID NO. 3 | siRNA1253 sense strand | GGACUUUGAUACAAUGUCA |
| SEQ ID NO. 4 | siRNA1253 anti-sense strand | UGACAUUGUAUCAAAGUCCAC |
| SEQ ID NO. 5 | siRNA2082 sense strand | CAUUGUUUCUGGUUAUUAA |
| SEQ ID NO. 6 | siRNA2082 anti-sense strand | UUAAUAACCAGAAACAAUGGC |
| SEQ ID NO. 7 | siRNA248 sense strand | GAGUAAAGAUGAUCUUGAA |
| SEQ ID NO. 8 | siRNA248 anti-sense strand | UUCAAGAUCAUCUUUACUCAA |
| SEQ ID NO. 9 | siRNA1019 sense strand | GAGAUUUGAUGGUAAGAAA |
| SEQ ID NO. 10 | siRNA1019 anti-sense strand | UUUCUUACCAUCAAAUCUCCA |
| SEQ ID NO. 11 | Modified siRNA1864 sense strand | GmsGmsUmUmAfCmUfGfUfAmGmUmUmCmAmCmAmAmAm |
| SEQ ID NO. 12 | Modified siRNA1864 anti-sense strand | UmsUfsUmGmUmGfAmAfCfUmAmCmAmGfUmAfAmCmCmsUmsCm |

TABLE 1-continued

| SEQ ID NO. | Description | Sequence |
|---|---|---|
| SEQ ID NO. 13 | Modified siRNA1253 sense strand | GmsGmsAmCmUfUmUfGfAfUmAmCmAmAmUmGmUmCmAm |
| SEQ ID NO. 14 | Modified siRNA1253 anti-sense strand | UmsGfsAmCmAmUfUmGfUfAmUmCmAmAfAmGfUmCmCmsAmsCm |
| SEQ ID NO. 15 | Modified siRNA2082 sense strand | CmsAmsUmUmGfUmUfUfCfUmGmGmUmUmAmUmUmAmAm |
| SEQ ID NO. 16 | Modified siRNA2082 anti-sense strand | UmsUfsAmAmUmAfAmCfCfAmGmAmAmAfCmAfAmUmGmsGmsCm |
| SEQ ID NO. 17 | Modified siRNA248 sense strand | GmsAmsGmUmAfAmAfGfAfUmGmAmUmCmUmUmGmAmAm |
| SEQ ID NO. 18 | Modified siRNA248 anti-sense strand | UmsUfsCmAmAmGfAmUfCfAmUmCmUmUfUmAfCmUmCmsAmsAm |
| SEQ ID NO. 19 | Modified siRNA1019 sense strand | GmsAmsGmAmUfUmUfGfAfUmGmGmUmAmAmGmAmAmAm |
| SEQ ID NO. 20 | Modified siRNA1019 anti-sense strand | UmsUfsUmCmUmUfAmCfCfAmUmCmAmAfAmUfCmUmCmsCmsAm |
| SEQ ID NO. 21 | First forward primer for RT-PCR of Ugt2b1 gene | GGACCGAGCTGTCTTCTGG |
| SEQ ID NO. 22 | First reverse primer for RT-PCR of Ugt2b1 gene | CACACAGACCAATAGGAACCC |
| SEQ ID NO. 23 | Second forward primer for RT-PCR of Ugt2b1 gene | GTGCTGGTGTGGCCTACAG |
| SEQ ID NO. 24 | Second reverse primer for RT-PCR of Ugt2b1 gene | ATTGCTCGGCCCAATGAGG |
| SEQ ID NO. 25 | Forward primer for RT-PCR of 36B4 gene | AACGGCAGCATTTATAACCC |
| SEQ ID NO. 26 | Reverse primer for RT-PCR of 36B4 gene | CGATCTGCAGACACACACTG |
| SEQ ID NO. 27 | Ugt2b1 gene sequence | GCAAGATGTCTATGAAACAGGCTTCAGTTTTTCTGTTGATACA<br>GTTCATATGCTATATTAGACCTGGAGCCTGTGGGAAAGTGCTG<br>GTGTGGCCTACAGAATACAGCCATTGGATAAATATGAAAATAAT<br>CCTGGATGAACTTGTCCAGAGAGGTCATGACGTCACCGTTCT<br>CATATCTTCTGCTTCCATCCTCATTGGGCCGAGCAATGAATCT<br>TCTATTAATTTTGAAATTTATTCTGCACCTTTGAGTAAAGATGAT<br>CTTGAATATGCTTTTGAAAAATGGGTAGGAAACTGGACATACG<br>AATTAAAAAAACTTCCATTTTGGACATCTTATTCAAAACTGCAA<br>AAAATCTCCAGTGAATATTCAGACATGATTGAAAGTTTCTGCAA<br>AGCAGTAGTTTGGAACAAGAGCCTCATGAAAAAACTCCAAGG<br>ATCTAAGTTTGATGTCGTTCTAGCAGATGCCTTGGTTCCCTGT<br>GGTGAGCTGCTATCAGAACTGCTTAAGACACCTTTAGTATACA<br>GTCTCCGCTTCTGTCCTGGATACAAATGTGAAAAGTACAGTG<br>GGGGCCTTCCACTCCCCCCTTCCTATGTGCCTGTGGTTCTGT<br>CAGAACTAAGTGACCACATGACATTTGCAGAAAGGGTGAAGA<br>ATATGTTGCAGGTGTTGCTTTTTGACTTTTGGTTTCAAACATTT<br>AACGAGAAATCCTGGAATCAGTTTTACAGTGATGTTCTAGGTA<br>AACTGTGCCTTTCATTGTTACTGTGAAATCCTGACTTGATGTTT<br>TTTTGAATGAGAATGTGTATAGGTGAATATAAAGGCATAGAATG<br>AGATTCTTAATTGTGAGCTGATAGAGTAAAAATAGAAGAGAATC<br>AAATAGGCTCTTAGCAAGGCAAAATACTGCAGAGTAATTATACA |

TABLE 1-continued

| SEQ ID NO. | Description | Sequence |
|---|---|---|
| | | GAACACTTCAGAAATTACTAACCATGCAAAATTAGACAAGGAA |
| | | GATTTCTCTTGGTGATCATTTGATCTGCTCTACATTGTCTAAGT |
| | | ATAAGAAACTCCAGGTTTCATTGAGTGCTTTAATATCTGTAAAT |
| | | GAGAACACTACAGAGTCATAATTCATTACCACAACTATTTGTGT |
| | | AGCACTGAAGAAAACACATTTCCTTAAGACATTTACTCACTTA |
| | | GAAATTAAAACATTTATCAAGAATGTCCTGAAAGCTTATTCACA |
| | | ATTAAATTGTACCACTAGAACCAGAAACAGTCAAGGCAACTTG |
| | | ATTTTCTTAGAATTTGAGTTGGATCATATCTATAAAACTTAATCT |
| | | TAAAGCCTTAAATCTTGATAGAAATGCATAGGTTTTTATTATTTT |
| | | CAAAATACCTTTTCATTAAATAAAATATTACCTAATTTATTAGGAG |
| | | AAACAGTTTAAATATTAACTGCTTATACAAATACCCAGCTATAAC |
| | | TTTGAGATATACAACTAAGTTAGTGATACTAGTCTCCTGTAACG |
| | | GACATAGTACAGCAGGGATAAAAGAAAATTAGTCATTCCTTAC |
| | | CAATTATCACATTGCATTTCAAGAATCAGAAACCAAAAGCATAG |
| | | CTACTAAAATGTGTAAAATAGACTAAATATTCTACAAAAGCTGT |
| | | GTTTCTAAGCATTTTCAAGCACCTTTGCAAGAGCAAAATTTCA |
| | | AATTTATTGGTGCAACGTTGGAAATCAATGTAATTTTCACACAA |
| | | TATTTATGTTAATACAATTATATCATAAATCATAACTGGAACATTT |
| | | TAAATTGCTTGTCTACATGACCTCAACTCATTGCAGAAATCACA |
| | | TGCTTTATTCCAGACAAACTCCTTTCACCATAGTGTATTTGTTT |
| | | TTGGTTTTGGGGTGCAGGGAGACCTACAACATTAACTGAGAT |
| | | GATGGGGAAGGCAGACATATGGCTCGTTCGAACCTTCTGGGA |
| | | CTTGAAATTTCCTCACCCTTTCTTGCCTAATTTTGACTTTGTTG |
| | | GAGGACTCCATTGTAAACCAGCCAAACCACTGCCTAAGGTAA |
| | | CTCTACATTGTTTCCCTTGGTAAACTGTTTTTCCTTTTCATGGA |
| | | AACAATTCTTAACCACTATTTCCAGATGTTTGGTTTTATGAAAC |
| | | ATATATCAAGTGGATTAGAACTCTCTGACAATTAAGATATACATT |
| | | ATTTCCTTACATCTCTGAATCTTCTTACTCTTAAGCAAAGTATTA |
| | | TACCACTTTAGAATGTGGTCAGTGATTTAAAGGTGTTTAGGTA |
| | | ACTCATAAAAGAGAATTTATGCTCTCTTCAAGAACATATAGTAA |
| | | ATGCCAGAGACGTGTTGAACAGCTAAAGAAATAAAGAATCAAT |
| | | ATCTTCACTAAATAGAAATTGTATTCTACTTGGAAACATTATAGT |
| | | GATGAAGAGATGTTATATACACTGTGACAAACGTTATACATTGT |
| | | TATATTAGATAAACAGATAAGTTGAAGATATATCCAACAGAGATG |
| | | AGATGTAATGTCCTAGAATCCTTGTGAAGTTACAATGACCTAG |
| | | CCAATGTACAGGGTTAGATTAATGAATGAAAAGAAGAGAGGAA |
| | | AAATAGAAAATTGAAACAACCATTGAAAGAATGACAGACTTAG |
| | | ATAAGCAGGACGATGACATGGCAGGCAGGAGTTTTTGGACAG |
| | | CTTCATGTATGCATGTTCCACACATGGCTCTCTTTTAACCTTTC |
| | | CACTTCCTTGGAGTCTTTCTACCCTTAGGTTCTGCAGGGATTT |
| | | ATTTTTTGTCTTTGTAGTTTCCACATGCAAAAGAAAACAACACT |
| | | TATCTTTCTGTTTCTGGCTTATTGATTAATCTCCTGTCCTCTAAA |
| | | CAATAGCTATTTTCCTAAATTATTTAATAATAATAACATTTTTCTAT |
| | | CTGAGTAAAACACAATTATGTATATTTACCAACACTTTGATACA |
| | | CATTGATCACTTGAAGAATATCTAAGCTAATCCTATATAGGGGA |
| | | ATTTTGAATAATGATGTAATAAACATTATTATGTAGATTTTTCACT |
| | | TGCAATTATTTCCTTCAGATATCACCAAAGAGTGGCATAGGTTA |
| | | ACTGTATGTAACACATTAATGTTATTTATATCAAGACGCTTATTT |
| | | ATGTATTTTATCTAATTTTACATTTCCAAATATGATAAATGCATAA |
| | | ATGTTCAATTTCCATATTATCTGTAGGAGCATTTTTATAGTACAT |
| | | ACATTTTTGTGACATTCATGATAAGTGGATTATGATGGAATATT |
| | | GATATATTTTGAATTTATTTTTTTAATAGCTGACATTATTGAAAGA |
| | | TTTTCAGATAATTGTAAGCTATTTAAATCTGAGGGAACAACTAC |
| | | TTTGGATCATTTGCCTAAGTTAATTGAATTCTTATTTCTTCTGAT |
| | | GTTAGTTTGTTTTTTTAATTAGCATACTCTCTTAAAAATTTATGA |
| | | ATATTACACAACTCTTTAGAGAGTCTCTTCATTTTGATAGATTTT |
| | | TTTGTTCTTCATAAGCTTTTACTATAAGGTACTCCTATTTTTCAA |
| | | TTCCCAAATTACTCCCAATGCTACTGTGGTTATTCAATACATTA |
| | | CTGCTTTTTATTCTATGTCATGGAGTTTCTCTTCTTTTTTCCCTA |
| | | TTTTTATGTAGTAGAAACACATTACTTTTATTTAGAATGTACTAA |
| | | AGATAATTTCTTTTTTTTCAATGTGAGAATACATAATTTTTTCAAT |
| | | TAATTAATTTATTTATGCCCCAAATGTTGCCTACATCGTGGTCC |
| | | CCCTCTTAGAGTTCTTCTCTATCCCTCATCTCCCTCTATCTCTC |
| | | CTTCCCTACATTTCTTCTTCTTTTCTATTCCCTCCTTTGCTGCT |
| | | CGTCCTTCTCATTTCTCTCAAAGAAACCACAAAAAAGAAAATC |
| | | AAAGAAATGAACTTAAAAAAATAAGACCAAAAATATTCCAGCAA |
| | | AACGAAAGGAAAGAAAAAGCACACATAAGATTTAATATAAATAA |
| | | ATAAATAAATAAATAAATAAATAAATAAAAACATGGCATTTATTTT |
| | | AGGTGGCTAACTATTCCTGGGCTTGGGACCTCCTCTGGTGTA |
| | | TGATTGATTTACCCAGTCACTACTGGGGAAAGCTGGTTTTCCC |
| | | CTTTGTTATCAGATACCACTTGCAAATAGCTTCTTAGTTAGAAG |
| | | TGGAAGTCCATGAACATTTTCTATTCTGTGCGCAGGAACTTCA |
| | | TCTGCCTTGAACCTGGGCAGGTCTTAGACATGCTGCTACAGT |
| | | CTCTGTGAGTTTATATGAGCATCAGTCTTATTATGCCTGGTAGA |
| | | CCCTGGGATGTCATTCATCCCCTCTGGATCTTATAAACTTTCT |
| | | CCCTCCTACTCATGATGGTTTGAAAATACCTCCTAATGAAACT |
| | | CTAAATTTCAATAACTCTACTGACAATAATTTTTTACTCTAATTTT |

TABLE 1-continued

| SEQ ID NO. | Description | Sequence |
|---|---|---|
| | | CTTATGTTGGTAAATTGTACTATAGCACAAATGTACTCTCCATG<br>AACACATGACTGCTGAGGCAATGGATACACTGGTCTCACTAA<br>AATAATTCCAGTAATTACATTATTTCCTCTGGTAATGTTTGTCTC<br>AGTTCCTTAGACAGTGCTTCCCAGGCAGCCATTAATTTGTGAT<br>GTCACAACTGTCTTCATAGGAAATGGAAGAATTTGTTCAGAGC<br>TCTGGAGAACATGGTGTGGTGGTGTTTTCTCTGGGATCAATG<br>GTTAAAAACATTAAAGAAGAAAAGGCCAATGTAGTTGCTTCTG<br>CTCTTGCCCAGATTCCACAGAAGGTAACATAAAGAGTTCACTG<br>GGTGGACAAATGTATTGTAAGTCTATTGAACTCTGAAAGGATT<br>GCAGTAGGAAAAACTGCTGTGAAATATAAAGTAAGGGGTTCTT<br>TCCTATGAATCTCAAACACCACATTAAAAAGAAAAGAATGAATT<br>GCAGAAGATAAAATATTAGTCTGGTTCTGATTGACATTATAACC<br>TGAAGGATCACACTTAGATCCAGCATGGTTGTGCATACCTGAC<br>CTGTTGGAGCTTAAAGAGCTGAGGTAGGTCTTTTTCTTCATAT<br>TTACAACCAGTTTACACTTCATGTTGATTCCCAGGCTTTTCTG<br>AGTCATTCAGTGTGTCAGTGTCTCAAAAGGAGAGAAGTAAAA<br>GAAAGAAAGGATGGAAGGAAGGAGAAACAGAAGGGAGATGT<br>ACAGTTATGAGGAATATTATGCTGAGGCTGGAAAGGTGCCTCA<br>GTGATGCATTAAGAACACAGGCTGCTCTTCCAGAGGAACTGG<br>ACTTGATTGCTAGGACTTACATAGTAGCTCATAAGTATCCCCAA<br>CTCAATTGCCAGGGAATCTCATGTGTTCTTCATGCCCCAGACA<br>GAACAGTCACAGTGCATGCACTGAATTACATGCAGGCAAAAG<br>ATCATATACATAAAATGAAACAAAAATATCTGTAAAGAAAGAGG<br>AAAATATCTTCTTGCCAGTGACTGATGTAGGAAAACATAAGAG<br>AAAAGATAAAAAAAATAGGTGCTGACTCTGCAGTGAACTCAG<br>GATTATAAAATTATGAACTCATCAACAGGAACTATGCTTCTAGC<br>ACATCAGATAAACATGTTTTTCTGGATGGTGAAAGAGGCTGTA<br>ATTTAAGATGGAGTCTTATGTAAGCAAGGACAGTGTGGGAAGA<br>ATCCAGCAGCTCCCAACGTCATAAACTCTATTGTTGAATTACTT<br>CCTAAAAGCAGAAGTCTTTTGATGTTTGTAAACTACATTTACTC<br>TATTACTTGATACTGATACCGCCTATTGTGGAGATAATTTTTTAT<br>CTTACAAAACACAAAGCATACAGAAAGTAAAGACTGACAGTTA<br>TTATTCCAGTTTGTGAAACTTCCTTGTACGTTAGAACTCAGTTT<br>GATACTAGACATGAAATGTATTCAGGACAATTCAAAGCATATTT<br>TCAATTTTCCTATTGACAATTGTTTCTTTTTTGTTTTTGTTTTTG<br>TTTTTGAGACAATTTTTCATGGACAGTCGTTAATAGACTTTATC<br>TGAAATGAAGCATACTTGCTAGTAAGAAAGAAATTATTTTTAGA<br>AATGGGAAATTATATCATGGTATATTATGAATCAAAATAAACCTA<br>ATTATAATGAATAGCTGAAAGAACACGGAAATATAGGTAAAACT<br>ATGTGGCTATGATTTTAAAAGATGCAATATTGAGATTATATGTAA<br>TATTTACATATATCCTATATATAGGATTATATATGAAATATACATAAT<br>CACATAATCATAAAATATTACTAATTTAACACTGTTTTCCCAGTA<br>AGGATTATATTAACTCTCTAAAAATGTCATGTATACAAGAATTTG<br>TCGTTAATTATCAGATATATAAAAATTGTAACACAGAAGTGGAT<br>GCTCACAGTCAGCTCTTGGATGGATCACAGGGCTCCCAATGG<br>AGGAGCTAGAGAAAGTATCCAAGGAGCTAAAGGGATCTGCAA<br>CCCTATAGATGGAACAACATTATGAACTAACCAGTACCCCAGA<br>GCTCTTGACTCTAGCTGCATATGTATCGAAAGATGACCTAGTC<br>GGCCATCACTGGAAAGAGAGGCCCATTGGACTTGCAAACTTT<br>ATATGCCCCAGTACAGGGGAACACCAGGGCCAAAAAGGGGG<br>AGTGGGTGGGTAGGGGAGTGGGGGGCGGTATGGGGGACTT<br>TTGGGATAGCATTGGAAATGTAAATGAGGAAAATACCTAATAAA<br>AAATTAAAAAAACAGAAATTTTAAAAAATGTATAATTAAATGGCA<br>TGCTCAAGTTATTAGGAAGCCATGTATAGAAAATGTATTATTTAT<br>TTCAGTCTTTTAATATCTCATACTAGTTTAGATTTCCCTTCTATTA<br>AATTTTATAGTCCATCATCTGGATAATGTTCAACTGAGTAATCT<br>CAATTCTCTAGAATCAAAATATGCCAAAGCCTTGGATTTCTTTA<br>ATTAAATAAGGTAGTGTCTGTGTGTAACAGGTTCTGTGGAGAT<br>TTGATGGTAAGAAACCAGACACCTTAGGATCCAACACTCGGC<br>TCTACAAGTGGATCCCCCAGAATGACCTTCTTGGTAAGGCAA<br>AGTTCCACTACAGCTTTGGGGCTATAGTAATATACTTATTTGAG<br>AACAGCCCCCTTCTGAGCCTTCATATTCCCCCTGTCTTTAATAT<br>TATGATCAATAATTATGTAAAACTTCTTCTCACTGCAGGTCATC<br>CAAAAACCAAAGCTTTTATAGCTCATGGTGGAACCAATGGCAT<br>CTATGAGGCGATCTACCATGGCATTCCTATTGTTGGTATTCCCT<br>TGTTTGGGGATCAACCTGATAATATTAACCACATAGTAGCCAA<br>GGGAGCAGCTGTTAGAGTGGACTTTGATACAATGTCAACTAC<br>AGACCTTCTCACTGCCTTGAAGACTGTCATTAATGACCCTTCG<br>TGAGTCTATTTGTTGTTTGTTTCCTTGTTTGAAGTTGTTTTGGT<br>TTTTTTTAAGGTTTTTTTTTCTTTTCTTTTCTTTTTTGTTTTGTAC<br>TATGTAACCACAAGACCAGCCAATAACTGATATAGGTCTGCTT<br>GCTTCTGTCTCCTGAGTGCTAGAATTAAAACTATGTGCATTCA<br>CGCTTGATGGTGAATAACTATTCCTTTGAAAATATTGCTAGATT<br>CACAACATCAGATTGATTTTTATCCTATTTGAAGGAGAATAATTT<br>TGAATAACTTTGTGATATTGCATGTCTGAAATATGTGCTTACTTT<br>AACAATAAAGATACCTTGAATTTAAGTTTCAATAAATGAGACAT<br>GATAAGTCTTAAACTATTCTATATACATAAATAATATCACAAATAT |

TABLE 1-continued

| SEQ ID NO. | Description | Sequence |
| --- | --- | --- |
| | | ATGTCTATTGGTAACAAGGACACTATTTCAAGATAGAATGTACA |
| | | TAGTATTCATGAACCATGATCTTAAATGAAAAGTTAAACATTTAC |
| | | CCATATTTTCTGAAGTTATAAAACTTTTGGTAAAACTTTAATTTC |
| | | TATAATGATATGTGATATTGCATAACCAGTACTGAAGAAATGAG |
| | | AGAGAGTATTAAATTATTACCATACCCAGAGAACACTGTTGGTA |
| | | GTTTCAAGGTATTCCAATAGACAAATGTACCTAATGAGAATATC |
| | | CAGAGGCAAAATAACAGGAGAAAGTGCACCTGGTTCTTCCAT |
| | | ACACAGTCTCCTAGTCCAGGAACACAATTACATTGCTTTCCAT |
| | | CCAGTCAGAAGTCTGCTGGAAATTCTGTTCAAGGAAGAATAAT |
| | | AACTTAGCAAGTGTTTTCAAAACATGAATCTGATTATAAAAAGA |
| | | AATTAGGAAACAGAGATAGAAGAGAAGAGGAGAAACCAAAAC |
| | | TAGAGAGGAGATATCCAGCATGAGATATGACCCTGTAGAGTTT |
| | | AAAAGAATTCAGTGTCCACTTCTTTTCTTAAAACTTACACACAC |
| | | ATACACACACACACACACACACACACACACACACTTTCTCTTG |
| | | CCAATGTTTGAAATATTGCTCAACTTCAAATTAAAAATAAGTATT |
| | | CTATGGGGAATAAAGCAAAAATAAGCCAAGTGTACCTGAGGA |
| | | GCTGGTATACAAGGTAAGCTCATTAGTTGGAGGTAAATTCAGG |
| | | ACTTCATTAAGACCAGTGTCAACTACACACCAAGTTCAAAAAA |
| | | AAACCTGTACTAAACAAGACTGTTTCACTGACTTCCCTGTCAC |
| | | TCAACTGTCCTCCCTATCACCTCATAAAACATAGTACTTGTGTG |
| | | GGAAGTTTATGCCATTCATTTTGAGACTCTTGTGGGACTTTTC |
| | | CCCAAACCAATAAATGTTAGGGAAGTCGACAAATTAGCTTTAA |
| | | TTTTAGTTGCATGCATTGTCCTTTCAGCTATAAAGAGAATGCCA |
| | | TGAGATTATCCAGAATCCACCATGACCAGCCAATGAAGCCCTT |
| | | GGACCGAGCTGTCTTCTGGATCGAGTATGTCATGCGCAACAA |
| | | GGGAGCCAAGCACCTTCGCCCAGCTCTGCATGACCTTACCT |
| | | GGTTCCAGTACCACTCTCTGGATGTGATTGGGTTCCTATTGGT |
| | | CTGTGTGGTAGCTGTGGTATTCATCATTGCAAAATGTTGCCTC |
| | | TTTTGTTGCCATAAGACTGCTAACATGGGAAAGAAGAAAAAAG |
| | | AGTAGCTTCATGAAGGCTGAAGCAGAGAGTCCTGAGAGATGA |
| | | GCCTCTGCCAGCTGCTTCCAGCAGAAACCTGTTGTCTGTCCC |
| | | AGGTGCCTTCCCTCTGAAACAAGACAGGGTCAGGACTTCATT |
| | | AAAGATAGCTCTCATAGATGCACTATATGTTGAATGCACGTAAG |
| | | GATTTATGCAAGCTATACACTCAGAGCTCTAGAAGCAAAATTG |
| | | TGTGTTCAGTTTAGAATGTTTTAATGTAAATGAGGAACTATACC |
| | | CAACAACAATCACTGAGGTTACTGTAGTTCACAAAATTTGCAT |
| | | AGGCATAAAGCCTTTGAAAAACCTCTCTAAATATTAGTTAATTT |
| | | TTTATGCTCTGTCTTCATTTAATGAACTTATTTTTCTTCCCTTCC |
| | | TTTTTTCTTCTCTTTCATTTTTTTTTGTATTGCTCATAAATAATAG |
| | | CGTTCAGGTACAGAACATTTGAAATAGACTCACTTTTCCATCA |
| | | ATATAAGGAAAGCCATTGTTTCTGGTTATTAATTGGGTACAGCA |
| | | AACTTCCAACAAATATTTCCTAAAGGGCCTGTGGTGGAGGCTA |
| | | CTCTCCTTCAATCAGAAGCCTTTTTCAGACACTAATCTTCAAG |
| | | CATTTACTCTTACTGCTCCTGACATAAATTCCAGTACTTGGGA |
| | | GTTCTTAGGCTTGGCAAGATTATTGATTTATTTTCCTTCTTATCT |
| | | CTTACTCACAACTGACCTGAACACTGTCATTCTCATTCTGCCT |
| | | TTTGAAGTAGATTTAAGCTGCCAAATGTCCCATTCTCTCTCGC |
| | | TTTGAAAGTACACATCCAAGAGAAGATTATCTTTTTAAGTCATA |
| | | CCATCACCTAGCTCATGTTATATTTCGTATCTGAAATATCCCCC |
| | | ACAGACACACAATGTACTTTGCTGATTTTGTTTAACTCATTCAT |
| | | ACAGAATTTCTTACCTTGATTCAATAAAATGTTAAAATCTT |

EXAMPLES

Methods

Treatment of ob/ob Mice 12 ob/ob mice (purchased from the Model Animal Research Center of Nanjing University, Nanjing, China) at 6 weeks of age were randomly divided into a control group (N=4) and an experimental group (N=8). ob/ob mice were mutant mice that ate excessively due to mutations in the gene responsible for the production of leptin and become profoundly obese. Overt hyperglycemia of ob/ob mice was observed during the fourth week. The blood glucose levels of the ob/ob mice rised to reach the peak after 3-5 months when the ob/ob mice had very high food intake and a rapid growth. Glucagon (300 μg/kg, Sigma-Aldrich, St. Louis, MO, USA) was administered by daily intraperitoneal injection for 14 days to ob/ob mice in the experimental group. Saline solution was administered to ob/ob mice in the control group in the same way. The saline solution-treated mice were used as a control. A glucose tolerance test (GTT) and an insulin tolerance test (ITT) were performed on the ob/ob mice in the two groups after stopping glucagon and saline solution administration.

Treatment of db/db Mice 12 db/db mice (purchased from the Model Animal Research Center of Nanjing University, Nanjing, China) at 6 weeks of age were randomly divided into a control group (N=4) and an experimental group (N=8). db/db mice were genetically mutated mouse in which leptin receptors did not function properly. The db/db mice were extremely obese and had many of the metabolic defects (such as, hyperphagia, hyperglycemia, hyperinsulinemia, and infertility). Glucagon receptor (GCGR) antagonist II (500 μg/kg, Merck Millipore, Massachusetts, USA) was administered by daily intraperitoneal injection for 14 days to db/db mice in the experimental group. Saline solution was administered to db/db mice in the control group in the same way. The saline solution-treated mice were used as a control. GTT and ITT were performed on the db/db mice in the two groups after stopping glucagon and saline solution administration.

GTT and ITT

The mice in the four groups fasted overnight for 16-18 h with free access to water in clean cages. For GTT, the mice were injected intraperitoneally with 1.5 g/kg body weight of D-glucose. Blood glucose was measured at a tail tip of each mouse using an ACCU-CHEK® Active blood glucose meter (Roche Diagnostics) at 0, 15, 30, 60, and 120 min post-injection. For ITT, the mice were injected intraperitoneally with insulin (Novolin® N Penfill®, Novo Nordisk, Bagsvaerd, Denmark) at a dose of 3 IU/kg for ob/ob and db/db mice. Blood glucose was measured at the tail tip of each mouse using an ACCU-CHEK® Active blood glucose meter at 0, 15, 30, 45, 60, 90, 120, 150, and 180 min post-injection. The area under the curve (AUC) was calculated using a standard method.

Next-Generation Sequencing and Data Analysis

Total RNAs were extracted from frozen tissues (e.g., fat, liver, and muscle) of each mouse following the Trizol RNA isolation procedure to perform RNA sequencing. The quality of input RNA was controlled by Agilent 2100, and only a sample with an RNA integrity number (RIN) no less than 7 was used. Total RNAs were then applied with poly(A)-positive RNA sequencing on Illumina Hiseq systems with 150 bp paired-end reads mode. RNA-seq reads were aligned to a reference genome by HISAT2 (V2.1.0) against the mouse genome annotation, which was downloaded by Ensembl. The fragments per kilobase of exon model per million reads mapped (FPKM) were measured by Stringtie (V1.3.4) with unique mapping reads. Differential expression analysis for the experimental groups (i.e., groups treated with glucagon and glucagon receptor antagonist II) and the control groups was performed using DESeq2 (V1.14.1) with gene count matrix obtained from Stringtie with the option '-e -B'. Briefly, genes with P-value less than 0.05 and padj-value less than 0.1 calculated by DESsq2 software were used as differential expressed genes. To generate heatmaps, Venn plot or other plots, 'heatmap', 'VennDiagram,' or 'ggplot2' in the R package were used.

Data Analyses

All data were analyzed using Igor Pro software (Wavemetrics, OR, USA). All data were presented as the means±s.e.m.; the number of mice used for each experiment was indicated. Statistical significance was evaluated using either Student's t-test for single Gaussian distributed datasets or the Mann-Whitney rank-sum test for non-single Gaussian distributed datasets. Labels of *, , and * represented significance less than 0.05, 0.01, and 0.001, respectively.

Example 1 GTT and ITT Results for ob/ob Mice and db/db Mice

Figure 2:
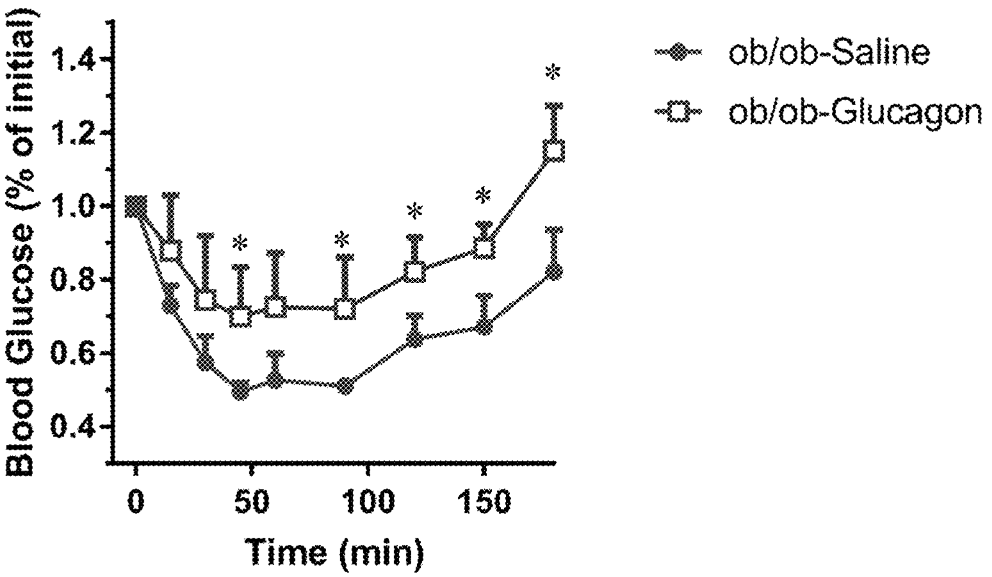
FIG. 2 is an analytical diagram illustrating blood glucose levels tested in ITT in ob/ob mice according to some embodiments of the present disclosure.

The mice were bred and handled for two weeks as described above. GTT and ITT results for ob/ob mice are shown in FIGS. 1 and 2. FIGS. 1 and 2 are analytical diagrams illustrating a GTT result and an ITT result for ob/ob mice, respectively. The ob/ob mice treated with glucagon were referred to as ob/ob-Glucagon, and the ob/ob mice treated with saline solution were referred to as ob/ob-Saline. As shown in FIG. 1, the blood glucose level of the experimental group for ob/ob mice is greater than that of the control group. Specifically, the blood glucose level of the experimental group is significantly greater than that of the control group at 0 min, 15 min, 30 min, and 120 min post-injection. The result suggested that the glucose tolerance of the ob/ob mice treated with glucagon is worse than that of treated with saline solution. As shown in FIG. 2, the blood glucose level of the experimental group for ob/ob mice is greater than that of the control group. Specifically, the blood glucose level of the experimental group for ob/ob mice is significantly greater than that of the control group at 45 min, 90 min, 120 min, 150 min, and 180 min post-injection. The results suggested that insulin tolerance of the ob/ob mice treated with glucagon is worse than that of treated with saline solution. The GTT and ITT results for ob/ob mice were consist with the glucagon effect of increasing the glucose level.

Figure 3:
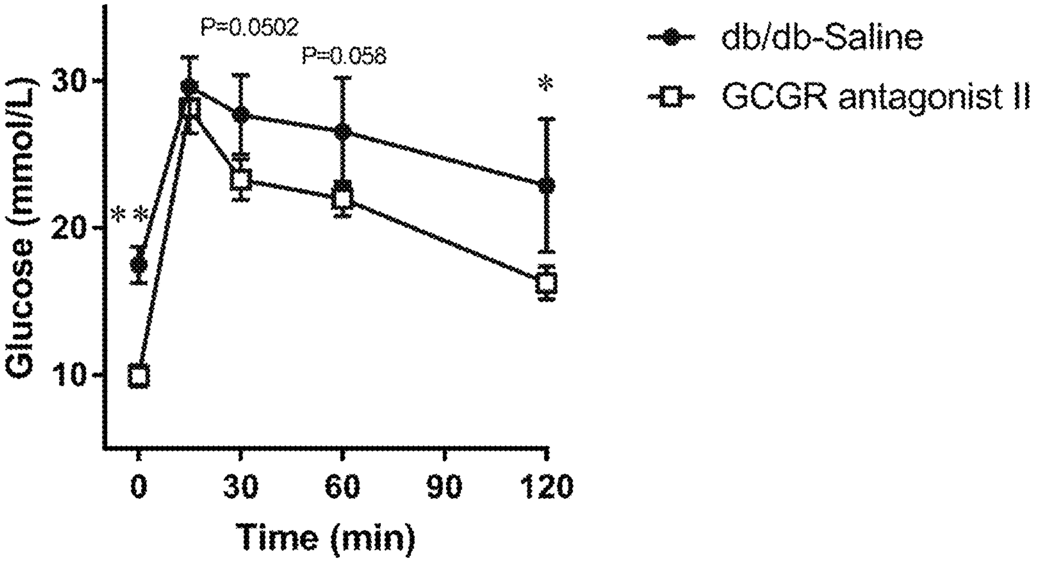
FIG. 3 is an analytical diagram illustrating blood glucose levels tested in GTT in db/db mice according to some embodiments of the present disclosure.
Figure 4:
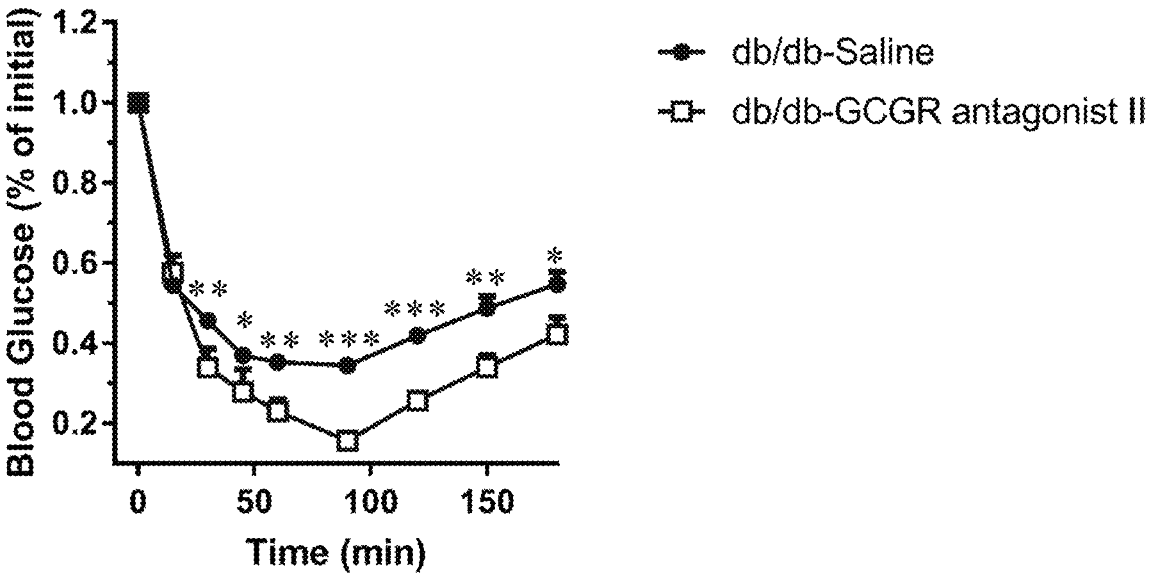
FIG. 4 is an analytical diagram illustrating blood glucose levels tested in ITT in db/db mice according to some embodiments of the present disclosure.

GTT and ITT results for db/db mice are shown in FIGS. 3 and 4. FIGS. 3 and 4 are analytical diagrams illustrating a GTT result and an ITT result for db/db mice, respectively. The db/db mice treated with GCGR antagonist II were referred to as db/db-GCGR antagonist II, and the db/db mice treated with saline solution were referred to as db/db-Saline. As shown in FIG. 3, the blood glucose level of the experimental group for db/db mice is less than that of the control group. Specifically, the blood glucose level of the experimental group is significantly less than that of the control group at 0 min and 120 min post-injection. The result suggested that the glucose tolerance of the db/db mice treated with the GCGR antagonist II is better than that of treated with saline solution. As shown in FIG. 4, the blood glucose level of the experimental group for db/db mice is less than that of the control group. Specifically, the level of blood glucose of the experimental group for db/db mice is significantly less than that of the control group at 30 min, 45 min, 60 min, 90 min, 120 min, 150 min, and 180 min post-injection. The result suggested that insulin tolerance of the db/db mice treated with the GCGR antagonist II is better than that of treated with the saline solution. The GTT and ITT results for db/db mice were consist with the effect of the GCGR antagonist II to decrease the glucose level.

Example 2 Determination of Target Genes for siRNA Treatment

Figure 5:
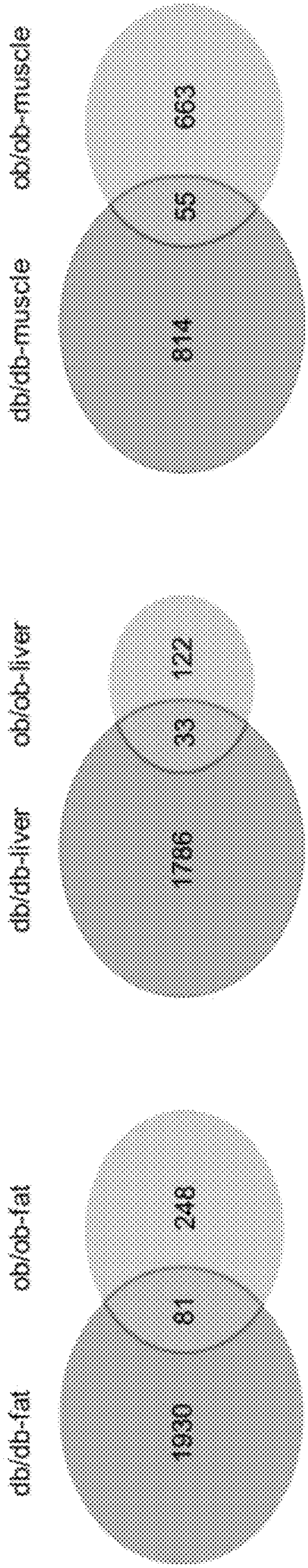
FIG. 5 is a Venn diagram illustrating overlapping numbers of differential expressed genes between ob/ob mice and db/db mice in three different tissues.

RNA sequencing was performed on frozen tissues including fat, liver, and muscle extracted from the four groups, of which the ob/ob mice treated with the glucagon and the db/db mice treated with the saline solution had diabetes onset and insulin resistance, and the ob/ob mice treated with the saline solution and the db/db mice treated with the GCGR antagonist II had not diabetes onset. Based on result of RNA sequencing, it was found that expression changes of genes were different in the mice with diabetes onset and the mice without diabetes onset. FIG. 5 is a Venn diagram illustrating overlapping numbers of differential expressed genes between ob/ob mice and db/db mice in the three different tissues, respectively. As seen from FIG. 5, the counts of differential expressed genes of db/db mice in fat, liver, and muscle were 1930, 1786, and 814, respectively. The counts of differential expressed genes of ob/ob mice in fat, liver, and muscle were 248, 122, and 663, respectively. As used herein, differential expressed genes of the db/db mice or the ob/ob mice refers to genes with expression changed in the experimental group for the db/db mice or the ob/ob mice compared with the control group for the db/db mice or the ob/ob mice. The overlapping numbers of differential expressed genes between the ob/ob mice and the db/db mice in three tissues, respectively, was 81, 33, and 55, indicating that these genes were changed in expression between the db/db mice and the ob/ob mice, and further suggesting that these changed genes was associated with diabetic metabolites.

Figure 6:
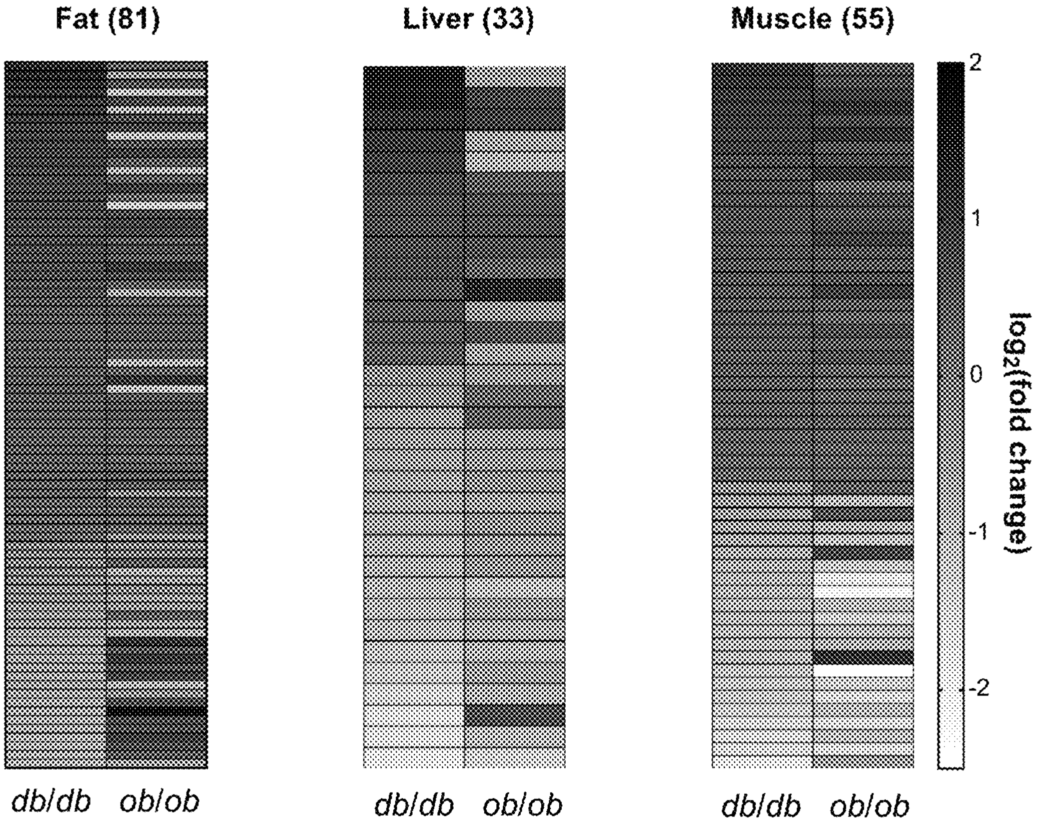
FIG. 6 is a heatmap illustrating a distribution of expression fold changes of overlapping genes in three different tissues of ob/ob mice and db/db mice.

To further investigate expression changes (e.g., improving or inhibiting) of these overlapping genes, expression fold changes of those overlapping genes were determined. FIG. 6 is a heatmap illustrating the distribution of expression fold changes of those overlapping genes in three different tissues of the mice. Among the overlapping genes, several genes with expression fold changes opposite in the ob/ob mice and the db/db mice were desired, of which a target gene, Ugt2b1, with expression fold changes increased in the ob/ob mice and expression fold changes decreased in the db/db mice was selected for siRNA treatment. Expression changes of Ugt2b1 gene in db/db and ob/ob mice after treatment were illustrated in Table 2.

TABLE 2

Expression changes of Ugt2b1 gene in db/db and ob/ob mice

| Gena Name | Group | BaseMean | $\log 2^{FoldChange}$ | IfcSE | pvalue |
|---|---|---|---|---|---|
| UDP glucuronosyltransferase 2 family, polypeptide B1(Ugt2b1) | db/db | 71.531 | −0.639 | 0.228 | 0.005 |
| | ob/ob | 63.416 | 0.799 | 0.235 | 0.001 |

In Table 2, BaseMean referred to an average value of Ugt2b1 gene expression in a control group (e.g., mice treated with the saline solution), FoldChange referred to the change in Ugt2b1 gene expression of the mice in the experimental group compared with the control group after treatment. Log $2^{FoldChange}$ greater than 0 indicated that Ugt2b1 gene expression was increased in the experimental group compared with the control group. Log $2^{FoldChange}$ less than 0 indicated that Ugt2b1 gene expression was decreased in the experimental group compared with the control group. FoldChange was determined by changed expression of the Ugt2b1 gene in the experimental group divided by that in the control group. IfcSE was log $2^{FoldChange}$ standard error. The p value was less than 0.05, indicating that there was a significant difference in gene expression before and after treatment. In conclusion, Ugt2b1 gene was associated with a blood glucose regulation path since the expression of Ugt2b1 gene was in a positive correlation with the blood glucose level in the mice. The Ugt2b1 gene was an effective and a suitable target for siRNA.

Example 3 Treatment of Different siRNAs in Cells 5 siRNAs named as siRNA248, siRNA1019, siRNA1253, siRNA1864, and siRNA2082 were designed for silencing the Ugt2b1 gene. The 5 siRNAs were modified chemically. The modified nucleotides of the siRNA included O-methyl modified nucleotides, fluoro modified nucleotides, phosphorothioate modified nucleotides. The modified sense RNA strand and the modified anti-sense RNA strand of the siRNA248 had a nucleotide sequence of SEQ ID NOs. 17 and 18, respectively. The modified sense RNA strand and the modified anti-sense RNA strand of the siRNA1019 had a nucleotide sequence of SEQ ID NOs. 19 and 20, respectively. The modified sense RNA strand and the modified anti-sense RNA strand of the siRNA1253 had a nucleotide sequence of SEQ ID NOs. 13 and 14, respectively. The modified sense RNA strand and the modified anti-sense RNA strand of the siRNA1864 had a nucleotide sequence of SEQ ID NOs. 11 and 12, respectively. The modified sense RNA strand and the modified anti-sense RNA strand of the siRNA2082 had a nucleotide sequence of SEQ ID NOs. 15 and 16, respectively. The 5 siRNAs were tested to determine the effect of inhibiting the expression of Ugt2b1 gene on Hepa1-6 of mouse hepatocarcinoma cells.

Hepa1-6 of mouse hepatocarcinoma cells were cultured in a 6-well plate and transfected with the 5 siRNAs, respectively, with scrambled siRNA Luciferase transfection as a negative control. The siRNAs were transfected into the 6-well plate by using Lipofectamine 2000 reagent adding 0.5-1 μg of siRNA per well. Then cells were cultured overnight (12 h) before next step. The transfected cells were collected to extract RNA for further RT-PCR. RT-PCR were performed to determine the relative expression of Ugt2b1 gene and a reference gene 36B4 treated by the 5 siRNAs using two pairs of primers for Ugt2b1 gene and a pair of primers for the reference gene 36B4. The two pairs of primers for Ugt2b1 gene had a nucleotide sequence of SEQ ID NOs. 21 and 22 and a nucleotide sequence of SEQ ID NOs. 23 and 24, respectively. The pair of primers for the reference gene 36B4 had a nucleotide sequence of SEQ ID NOs. 25 and 26.

Figure 7A:
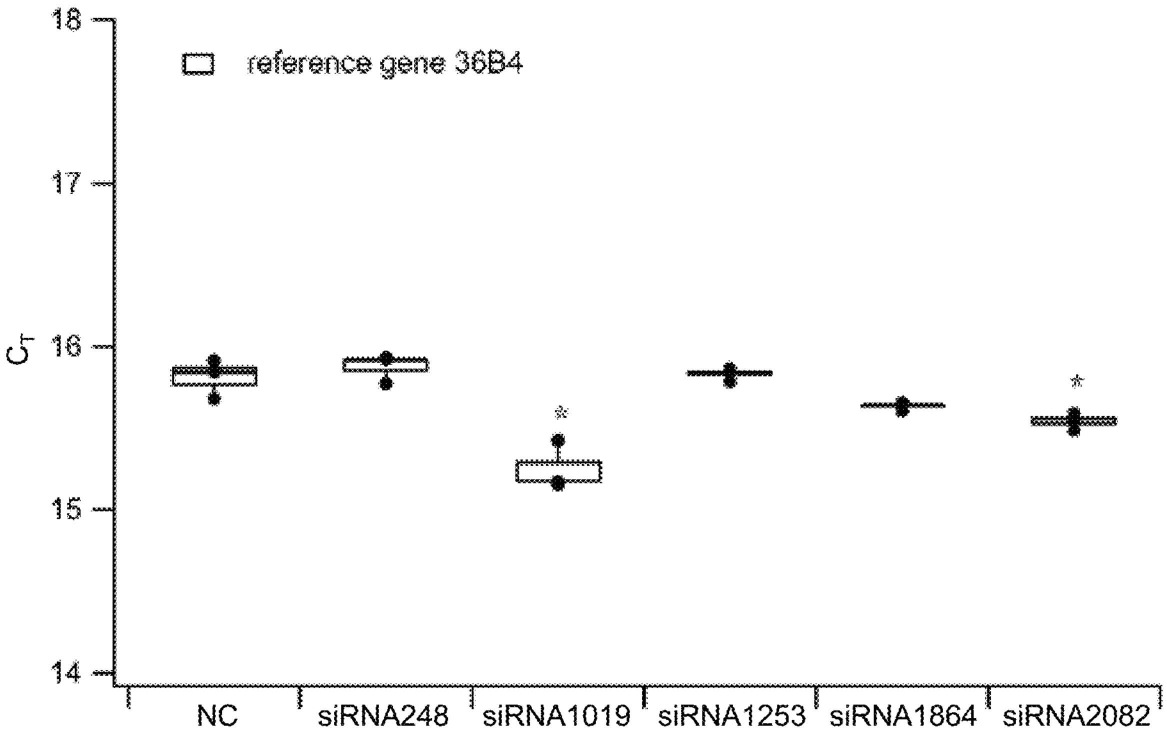
FIG. 7A is an analytical diagram illustrating $C_T$ values of reference gene 36B4 in a control sample and samples treated with 5 siRNAs.
Figure 7B:
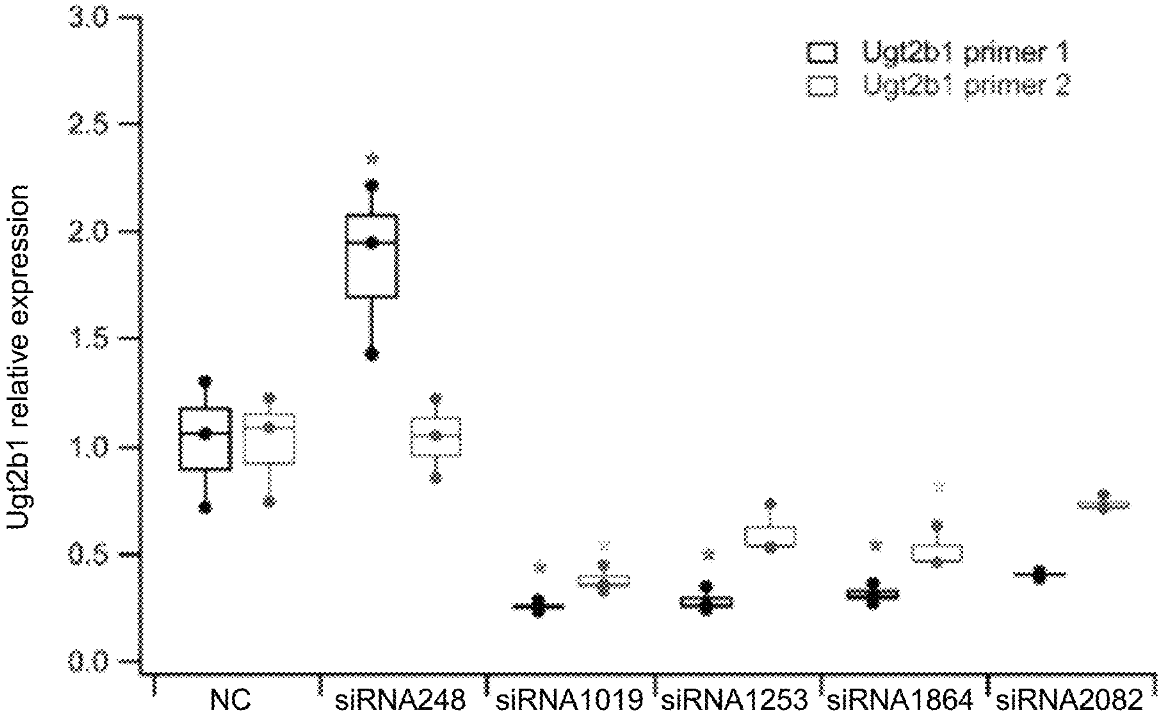
FIG. 7B is an analytical diagram illustrating relative expression of Ugt2b1 gene in a control sample and samples treated with 5 siRNAs.

FIG. 7A is an analytical diagram illustrating $C_T$ values of reference gene 36B4 in the control sample and samples treated with the 5 siRNAs. As seen from FIG. 7A, the $C_T$ values of samples treated with siRNA1019 and siRNA2082 deviated from the $C_T$ value of the control sample which was not treated with siRNA. siRNA248, siRNA1253, and siRNA1864 substantially did not affect the expression of the control gene. FIG. 7B is an analytical diagram illustrating relative expression of Ugt2b1 gene in the control sample and samples treated with the 5 siRNAs. As seen from FIG. 7, siRNA1019, siRNA1253, siRNA1864, and siRNA2082 inhibited the expression of Ugt2b1 gene except siRNA248. Thus, siRNA1253 and siRNA1864 effectively inhibited the expression of Ugt2b1 gene and did not affect the expression of the reference gene 36B4.

Example 4 Treatment of siRNAs in Mice siRNA1864 was selected to test in the db/db mice. 18 db/db mice at six weeks of age were equally divided into 3 groups, i.e., a first group, a second group, and a third group. The first group was administered with saline solution as a blank control. The second group was administered with a scrambled siRNA Luciferase as a negative control. The third group was administered with the siRNA-1864. siRNA was injected intravenously into db/db mice in the third group via a lipid carrier LP171. The mice were all kept for 4 weeks. The saline solution, the scrambled siRNA Luciferase, and the siRNA-1864 were administered with 1 mg/kg once every 5 days. Blood glucose level was detected and GTT was performed every two weeks. After the 4 weeks of the experiment, liver tissue of each mouse was taken to extract total RNA to test the silencing efficiency of siRNA-1864. Tissue samples from each mouse were tested independently three times to avoid experimental errors.

Figure 8:
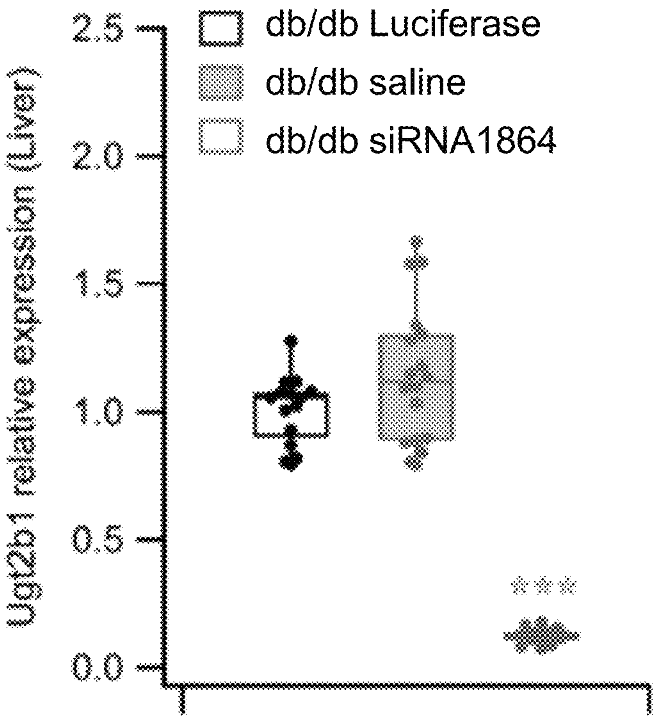
FIG. 8 is an analytical diagram illustrating relative expression of Ugt2b1 gene in control db/db mice and db/db mice treated with siRNA-1864.

FIG. 8 is an analytical diagram illustrating relative expression of Ugt2b1 gene in the control db/db mice and the db/db mice treated with the siRNA-1864. As seen from FIG. 8, siRNA-1864 significantly inhibited the RNA expression level of Ugt2b1 in the liver of db/db mice compared with the two controls.

Figure 9:
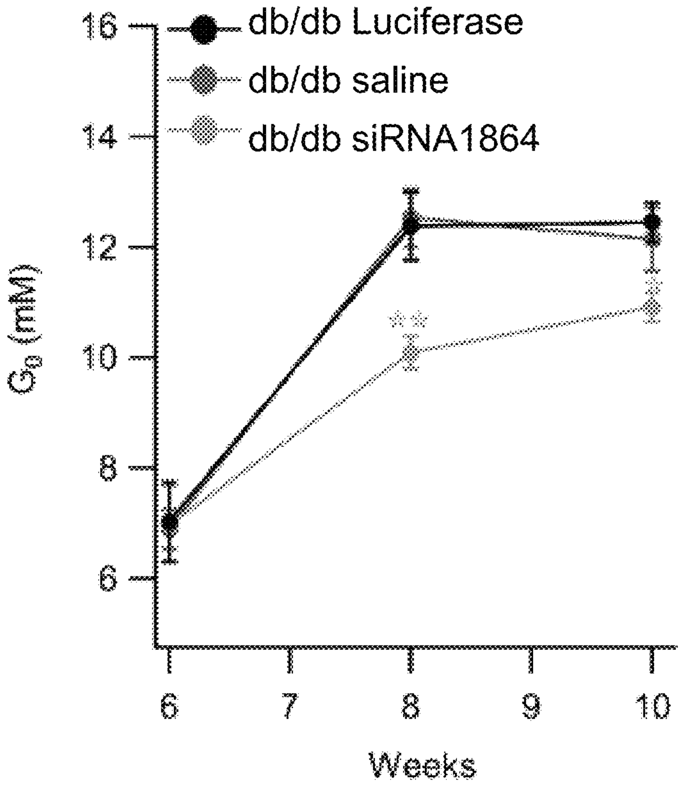
FIG. 9 is an analytical diagram illustrating resting blood glucose level (represented by $G_0$) in control db/db mice and db/db mice treated with siRNA-1864.
Figure 10:
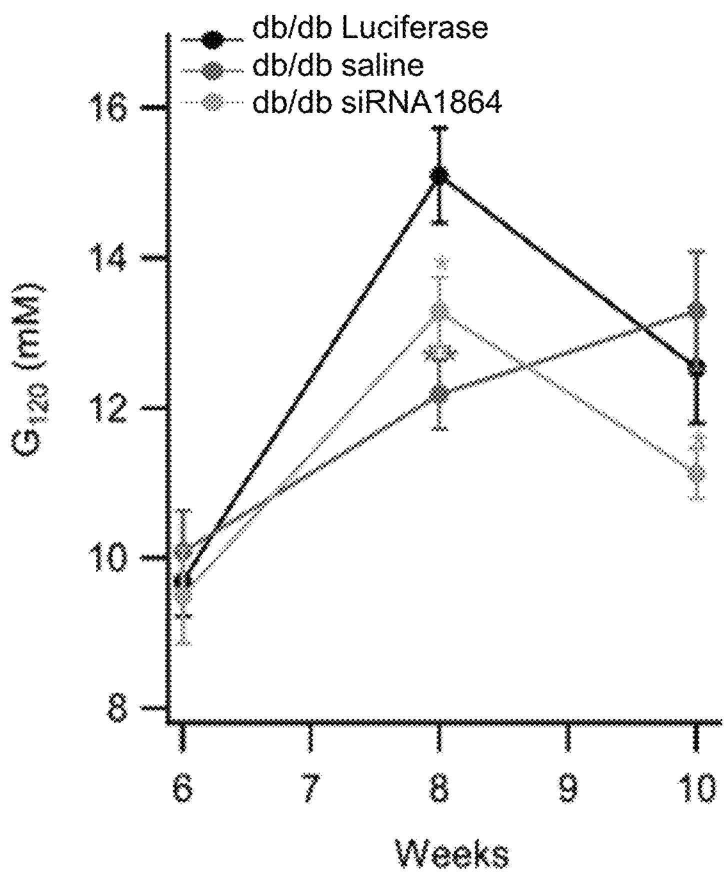
FIG. 10 is an analytical diagram illustrating 2-hour post-load glucose level (represented by $G_{120}$) tested in GTT in db/db mice and db/db mice treated with siRNA-1864.

FIGS. 9-10 are analytical diagrams illustrating resting blood glucose (represented by $G_0$) and 2-hour post-load glucose level (represented by $G_{120}$) tested in GTT in the control db/db mice and the db/db mice treated with the siRNA-1864. At the beginning of the experiment at the sixth week, there was almost no difference in blood glucose level in the three groups of mice. After treatment, the resting blood glucose level of the db/db mice treated with the siRNA-1864 was significantly reduced compared with the two control groups. Thus, siRNA-1864 targeted to Ugt2b1 gene significantly inhibited the RNA expression level of Ugt2b1 and effectively reduced the blood glucose level in the db/db mice.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure and are within the spirit and scope of the exemplary embodiments of this disclosure.

Moreover, certain terminology has been used to describe embodiments of the present disclosure. For example, the terms "one embodiment," "an embodiment," and "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "module," "unit," "component," "device," or "system." Furthermore, aspects of the present disclosure may take the form of a computer program product embodied in one or more computer-readable medium having computer readable program code embodied thereon.

Furthermore, the recited order of processing elements or sequences, or the use of numbers, letters, or other designations, therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software-only solution, e.g., an installation on an existing server or mobile device.

Similarly, it should be appreciated that in the foregoing description of embodiments of the present disclosure, various features are sometimes grouped together in a single embodiment, figure, or description thereof to streamline the disclosure aiding in the understanding of one or more of the various embodiments. This method of disclosure, however, is not to be interpreted as reflecting an intention that the claimed subject matter requires more features than are expressly recited in each claim. Rather, claim subject matter lie in less than all features of a single foregoing disclosed embodiment.

What is claimed is:

1. A short interfering RNA (siRNA) molecule comprising a sense RNA strand and an anti-sense RNA strand, the sense and anti-sense RNA strands forming an RNA duplex, and wherein the sense RNA strand or the anti-sense RNA strand is 15 to 25 nucleotides in length;

the sense RNA strand or the anti-sense RNA strand are 70%-100% complementary to a part of a nucleotide sequence of Ugt2b1 gene; and the sense RNA strand has a nucleotide sequence having at least 92% similarity with SEQ ID NO. 1, and the anti-sense RNA strand has a nucleotide sequence having at least 92% similarity with SEQ ID NO. 2; or the sense RNA strand has a nucleotide sequence having at least 92% similarity with SEQ ID NO. 3, and the anti-sense RNA strand has a nucleotide sequence having at least 92% similarity with SEQ ID NO. 4;

```
SEQ ID NO. 1:
5'-GGUUACUGUAGUUCACAAA-3';

SEQ ID NO. 2:
5'-UUUGUGAACUACAGUAACCUC-3';

SEQ ID NO. 3:
5'-GGACUUUGAUACAAUGUCA-3';
```

-continued

```
SEQ ID NO. 4:
5'-UGACAUUGUAUCAAAGUCCAC-3'.
```

2. The siRNA molecule of claim 1, wherein the sense RNA strand has a nucleotide sequence of SEQ ID NO. 1, and the anti-sense RNA strand has a nucleotide sequence of SEQ ID NO. 2.

3. The siRNA molecule of claim 1, wherein the sense RNA strand has a nucleotide sequence of SEQ ID NO. 3, and the anti-sense RNA strand has a nucleotide sequence of SEQ ID NO. 4.

4. The siRNA molecule of claim 1, wherein the sense RNA strand and/or the anti-sense RNA strand comprises modified nucleotides at about 25%-100% of nucleotide positions.

5. The siRNA molecule of claim 4, wherein the modified nucleotides include one or more of an O-methyl-modified nucleotide, a phosphorothioate-modified nucleotide, or a fluoro-modified nucleotide.

6. The siRNA molecule of claim 5, wherein the sense RNA strand includes a modified RNA strand having a nucleotide sequence of SEQ ID NO. 11 or SEQ ID NO. 13, in which "m" represents O-methyl modification, "s" represents phosphorothioate modification, and "f" represents fluoro modification.

```
SEQ ID NO. 11:
5'-GmsGmsUmUmAfCmUfGfUfAmGmUmUmCmAmCmAmAmAm-3'

SEQ ID NO. 13:
5'-GmsGmsAmCmUfUmUfGfAfUmAmCmAmAmUmGmUmCmAm-3'
```

7. The siRNA molecule of claim 5, wherein the anti-sense RNA strand includes a modified RNA strand having a nucleotide sequence of SEQ ID NO. 12 or SEQ ID NO. 14, in which "m" represents O-methyl modification, "s" represents phosphorothioate modification, and "f" represents fluoro modification.

```
SEQ ID NO. 12:
5'-UmsUfsUmGmUmGfAmAfCfUmAmCmAmGfUmAfAmCmCmsUms

Cm-3'
```

-continued

```
SEQ ID NO. 14:
5'-UmsGfsAmCmAmUfUmGfUfAmUmCmAmAfAmGfUmCmCmsAms

Cm-3'
```

8. The siRNA molecule of claim 1, wherein the siRNA comprises a double-stranded RNA including a sense RNA strand having 15 to 25 bases of Ugt2b1 mRNA and an anti-sense RNA strand complementary to 15 to 25 bases of Ugt2b1 mRNA.

9. The siRNA molecule of claim 1, wherein the siRNA molecule is configured to reduce UGT levels by inhibiting an expression of Ugt2b1 gene.

10. A medical composition including the siRNA molecule of claim 1.

11. The medical composition of claim 10, wherein the sense RNA strand and the anti-sense RNA strand form a hairpin structure.

* * * * *